United States Patent [19]
Murry et al.

[11] Patent Number: 5,817,480
[45] Date of Patent: Oct. 6, 1998

[54] DNA ENCODING A HISTAMINE H2 RECEPTOR

[75] Inventors: Lynn E. Murry, Portola Valley; Janice Au-Young, Berkeley; Karl J. Guegler, Menlo Park; Surya K. Goli, Sunnyvale, all of Calif.

[73] Assignee: Incyte Pharmaceuticals, Palo Alto, Calif.

[21] Appl. No.: 748,485

[22] Filed: Nov. 7, 1996

[51] Int. Cl.$^6$ ............................ C12N 15/12; C12N 15/66; C07K 14/705
[52] U.S. Cl. .................. 435/69.1; 435/91.41; 536/23.5; 530/350
[58] Field of Search ................................ 435/69.1, 91.4; 536/23.5; 530/350

[56] References Cited

U.S. PATENT DOCUMENTS 5,622,860   4/1997   Yamada et al. .................. 435/252.3

FOREIGN PATENT DOCUMENTS 2297328   7/1996   United Kingdom .

OTHER PUBLICATIONS

Spiegel, A., "G protein gene knockout hits the gut," *Nature Medicine*, 1:522–524 (1995).

Rudolph, U., et al., "Ulcerative colitis and adenocarcinoma of the colon in G alpha i2–deficient mice," *Nat. Genet*, 10:143–159 (1995).

Gantz, I., et al., "Molecular cloning of a gene encoding the histamine H2 receptor", *Proc. Natl. Acad. Sci.*, 88:429–433 (1990) (GI 163952).

Gantz, I., et al., "Molecular cloning of a gene encoding the histamine H2 receptor," *Proc. Natl. Acad. Sci.*, 88:5937 (1991) (GI 163952).

Gantz, I., "Molecular Cloning of the Human Histamine $H_2$ Receptor," *Biochemical and Biophysical Research Communications*, 178(3) 1386–1392 (1991) (GI 184088).

Traiffort, E. (GI 791239) GenBank Sequence Database (Accession U25440), National Center for Biotechnology Information, National Library of Medicine, Bethesda, Maryland 2084.

Ruat, M. et al., "Cloning and Tissue Expression of a Rat Histamine H2–Receptor Gene," *Biochemical and Biophysical Research Communicatons*, 179(3) 1470–1478 (1991) (GI 236184).

Hirasawa, A., et al., "Cloning, functional expression and tissue distribution of human α 1C–adrenoceptor splice variants," *FEBS Letters*, 363:256–260 (1995) (GI 927211).

Schmuck, K., et al., "Cloning and functional characterization of the human 5–$HT_{2B}$ serotonin receptor," *FEBS Letters*, 342:85–90 (1994) (GI 475198).

Erb, L., et al., "Functional expression and photoaffinity labeling of a cloned P2U purinergic receptor," *Proc. Natl. Acad. Sci.* 90:10449–10453 (1993).

Taussig, R., et al., "Expression and Purification of Recombinant Adenylyl Cyclases in Sf9 Cells," *Methods in Enzymology*, 238:95–108 (1994).

Gantz, et al. Bicohem. Biophys. Res. Comm. vol. 178 (3): pp. 1386–1392 (1991).

*Primary Examiner*—Stephen Walsh
*Assistant Examiner*—Daryl A. Basham
*Attorney, Agent, or Firm*—Lucy J. Billings

[57] ABSTRACT

The present invention provides a novel histamine H2 receptor (H2RH) and polynucleotides which identify and encode H2RH. The invention also provides genetically engineered expression vectors and host cells comprising the nucleic acid sequences encoding H2RH and a method for producing H2RH. The invention also provides for agonists, antibodies, or antagonists specifically binding H2RH, and their use, in the prevention and treatment of diseases in which H2RH is expressed. Additionally, the invention provides for the use of antisense molecules to polynucleotides encoding H2RH for the treatment of diseases associated with the expression of H2RH. The invention also provides diagnostic assays which utilize the polynucleotide, or fragments or the complement thereof, and antibodies specifically binding H2RH.

7 Claims, 14 Drawing Sheets

```
                                                        45        54
       9         18        27        36                TTG       CAG
5' G  GGA  CTG  ACT  AAA  TGT  CAG  CAA  GAG  GAG  AGT  CTC  ACC  CTG  CTT  AGG
                                                                                108
      63        72        81        90        99                               TGA
ATG  GCG  CGA  TCT  CGG  CTC  CTG  GGT  TCA  AGC  AAT  TCT  CCT  GCC  TCA  GCC  TCC 117       126       135       144       153                               162
ATA  GCC  GGG  ATT  ACA  GTC  GTC  CAG  CAT  GCT  CTG  CCC  ACC  CCA  CGC  CGA  GGT  GCA 171       180       189       198       207                               216
CTG  ACC  ATG  AGC  CTC  AAC  TCC  TCC  CTC  AGC  TGC  AGG  AAG  GAG  CTG  AGT  AAT  CTC
      M    S    L    N    S    S    L    S    C    R    K    E    L    S    N    L 225       234       243       252       261                               270
ACT  GAG  GGG  GAG  GGT  GGC  GAA  GGG  GGC  GTC  ATC  ACC  CAG  TTC  ATC  GCC  ATC
  T    E    G    E    G    G    E    G    G    V    I    T    Q    F    I    A    I 279       288       297       306       315                               324
ATT  GTC  ATC  ACC  ATT  TTT  GTC  TGC  CTG  GGA  AAC  CTG  GTG  ATC  GTG  ATC  ACC  TTG
  I    V    I    T    I    F    V    C    L    G    N    L    V    I    V    V    T    L 333       342       351       360       369                               378
TAC  AAG  TCC  TAC  CTC  CTC  ACC  CTC  AGC  AAC  AAG  TTC  GTC  TTC  AGC  CTG  ACT
  Y    K    S    Y    L    L    T    L    S    N    K    F    V    F    S    L    T
```

FIGURE 1A

```
            387             396     405     414     423     432
CTG TCC AAC TTC CTG TCC GTG TTG CTG CCT TTT GTG GTG ACG AGC TCC
 L   S   N   F   L   S   V   L   L   P   F   V   V   T   S   S 441             450     459     468     477     486
ATC CGC AGG GAA TGG ATC TTT GGT GTA GTG TGC AAC TTC TCT GCC CTC CTC
 I   R   R   E   W   I   F   G   V   V   C   N   F   S   A   L   L 495             504     513     522     531     540
TAC CTG ATC AGC TCT GCC AGC ATG CTA ACC CTC GGG GTC ATT GCC ATC GAC
 Y   L   I   S   S   A   S   M   L   T   L   G   V   I   A   I   D 549             558     567     576     585     594
CGC TAT GCT GTC CTG TAC CCC ATG GTG TAC CCC ATG AAG ATC ACA GGG AAC
 R   Y   A   V   L   Y   P   M   V   Y   P   M   K   I   T   G   N 603             612     621     630     639     648
CGG GCT GTG ATG GCA CTT GTC TAC ATC TGG CAC TCG CTC CTC ATC GGC CTG
 R   A   V   M   A   L   V   Y   I   W   H   S   L   L   I   G   L 657             666     675     684     693     702
CCA CCC CTG TTT GGT TGG TCA TCC GTG GAG TTT GAC GAG TTC TGG ATG CTG
 P   P   L   F   G   W   S   S   V   E   F   D   E   F   W   M   C 711             720     729     738     747     756
GTG GCT TGG CAC CGG GAG CCT CGG TAC ACG GCC TTC TGG CAG ATC TGG TGT
 V   A   W   H   R   E   P   R   Y   T   A   F   W   Q   I   W   C
```

```
     765         774         783         792         801         810
GCC CTC TTC CCC TTT CTG GTC ATG CTG GTG TGC TTC ATC TTC CGC GTG
 A   L   F   P   F   L   V   M   L   V   C   F   I   F   R   V 819         828         837         846         855         864
GCC GTC AAG GCA CGC AAG GTG CAC TGT GGC ACA GTC ATC GTG GAG GAG
 A   V   K   A   R   K   V   H   C   G   T   V   I   V   E   E 873         882         891         900         909         918
GAT GCT CAG AGG ACC GGC GTC AAG AAC TCC AGC ACC TCC TCT TCA
 D   A   Q   R   T   G   V   K   N   S   S   T   S   S   S 927         936         945         954         963         972
GGC AGC AGG AAT GCC TTT CAG GTC TAC TCG GCC AAC CAG TGC AAA
 G   S   R   N   A   F   Q   V   Y   S   A   N   Q   C   K 981         990         999        1008        1017        1026
GCC CTC ATC ACC ATC CTG GTC GTG GGT CTC GGT GCC TTC ATG GTC CCC
 A   L   I   T   I   L   V   V   G   L   G   A   F   M   V   P 1035        1044        1053        1062        1071        1080
TAC ATG GTT GTC ATC GCC TCT GAG GCC CTC TGG GGG AAA AGC TCC CCG
 Y   M   V   V   I   A   S   E   A   L   W   G   K   S   S   P 1089        1098        1107        1116        1125        1134
AGC CTG GAG ACT TGG GCC ACA TGG GCC CTG TCC TTT GCC AGC GCT TGC CAC CCC
 S   L   E   T   W   A   T   W   A   L   S   F   A   S   A   V   C   H   P
```

FIGURE 1C

```
            1143                1152                1161                1170                1179                1188
       CTG ATC TAT GGA CTC TGG AAC AAG ACA GTT CGC AAA GAA CTA CTG GGC ATG TGC
        L   I   Y   G   L   W   N   K   T   V   R   K   E   L   L   G   M   C 1197                1206                1215                1224                1233                1242
       TTT GGG GAC CGG TAT TAT CGG GAA CCA TTT GTG CAA CGA CAG AGG ACT TCC AGG
        F   G   D   R   Y   Y   R   E   P   F   V   Q   R   Q   R   T   S   R 1251                1260                1269                1278                1287                1296
       CTC TTC AGC ATT TCC AAC AGG ATC ACA GAC CTG GGC CTG TCC CCA CAC CTC ACT
        L   F   S   I   S   N   R   I   T   D   L   G   L   S   P   H   L   T 1305                1314                1323                1332                1341                1350
       GCG CTC ATG GCA GGA CAG CCC CTG GGG CAC AGC AGC CTG ACG GGG GAC ACT
        A   L   M   A   G   Q   P   L   G   H   S   S   L   T   G   D   T 1359                1368                1377                1386                1395                1404
       GGC TTC AGC TGC TCC CAG GAC TCA GGG ACA GAT ATG ATG CTG CTT GAG GAC TAC
        G   F   S   C   S   Q   D   S   G   T   D   M   M   L   L   E   D   Y 1413                1422                1431                1440                1449                1458
       ACG TCT GAT GAC AAC CCT CCC TCT CAC TGC ACT TGC CCA CCC AAG AGA AGG AGC
        T   S   D   D   N   P   P   S   H   C   T   C   P   P   K   R   R   S 1467                1476                1485                1494                1503                1512
       TCG GTG ACA TTT GAG GAT GAA GTG GAA CAA ATC AAA GAA GCT GCC AAG AAC TTC
        S   V   T   F   E   D   E   V   E   Q   I   K   E   A   A   K   N   F
```

FIGURE 1D

```
      1521      1530          1539          1548          1557      1566
GAT TCT TCA TGT GAA AGC TGA AGT ACA CAA GTC CTT GGA CAG TTA CGC AGC AAG
 D   S   S   C   E   S 1575      1584
CTT GGC CAA AGC CAT TGA GG 3'
```

| | | |
|---|---|---|
| 342 | G D R Y Y R E P F V Q R Q R T S R L F S | 1722180 |
| 300 | Q Q L F R - - C R P A S H N A Q E - - T | GI 163952 |
| 297 | Q Q L F C - - C R L A N R N S H K - - T | GI 1359759 |
| 300 | Q Q L F C - - C R L A N R N S H K - - T | GI 184088 |
| 300 | H Q L F C - - C R L A S H N S H E - - T | GI 791239 |
| 299 | Q Q L F H - - C K F A S H N S H K - - T | GI 236184 |
| 338 | Q N V L R I Q C L R R K Q S S K H - - A | GI 927211 |
| 392 | G R Y - - I T C N Y R A T K S V K - - T | GI 475198 |
| | | |
| 362 | I S N R I T D L - G L S P H L T A L M A | 1722180 |
| 316 | - - - - - - - - - - - - - - - S L R S | GI 163952 |
| 313 | - - - - - - - - - - - - - - - S L R S | GI 1359759 |
| 316 | - - - - - - - - - - - - - - - S L R S | GI 184088 |
| 316 | - - - - - - - - - - - - - - - S L R L | GI 791239 |
| 315 | - - - - - - - - - - - - - - - S L R L | GI 236184 |
| 356 | L G - - - - - - Y T L H P P S Q A V E G | GI 927211 |
| 408 | L R K R S S K I Y F R N P M A E N S K F | GI 475198 |
| | | |
| 381 | G G Q P L G H S S S T G D T G F S C S Q | 1722180 |
| 320 | N S S Q L A R N Q - - S R E P M R - Q E | GI 163952 |
| 317 | N A S Q L S R T Q - - S R E P R Q - Q E | GI 1359759 |
| 320 | N A S Q L S R T Q - - S R E P R Q - Q E | GI 184088 |
| 320 | N N S Q L N R S Q - - C Q E P R W - Q E | GI 791239 |
| 319 | N N S L L P R S Q - - S R E G R W - Q E | GI 236184 |
| 370 | Q H K D M V R I P V G S R E T F Y - R I | GI 927211 |
| 428 | F K K H G I R N - - G I N P A M Y - Q S | GI 475198 |
| | | |
| 401 | D S G T D M M L L E D Y T S D D N P P S | 1722180 |
| 337 | E K P L K L Q V W - - - - - - - S G T | GI 163952 |
| 334 | E K P L K L Q V W - - - - - - - S G T | GI 1359759 |
| 337 | E K P L K L Q V W - - - - - - - S G T | GI 184088 |
| 337 | D K P L N L Q V W - - - - - - - S G T | GI 791239 |
| 336 | E K P L K L Q V W - - - - - - - S G T | GI 236184 |
| 389 | S K T D G V C E W K F F S S M P R G S A | GI 927211 |
| 445 | P M R L R S S T I Q S S S I I L L D T L | GI 475198 |

FIGURE 2F

| | | | | | | | | | | | | | | | | | | |
|---|---|---|---|---|---|---|---|---|---|---|---|---|---|---|---|---|---|---|
| 421 | H | C | T | C | P | P | K | R | R | S | S | V | T | F | E | D | E | V | E Q | 1722180 |
| 349 | E | V | T | A | P | R | G | A | T | D | - | - | - | - | - | - | - | - | - - | GI 163952 |
| 346 | E | V | T | | | | | | | | | | | | | | | | | GI 1359759 |
| 349 | E | V | T | A | P | Q | G | A | T | D | - | - | - | - | - | - | - | - | - - | GI 184088 |
| 349 | E | V | T | A | P | Q | G | A | T | N | - | - | - | - | - | - | - | - | - - | GI 791239 |
| 348 | E | L | T | H | P | Q | G | N | P | I | - | - | - | - | - | - | - | - | - - | GI 236184 |
| 409 | R | I | T | V | S | K | D | Q | S | S | C | T | T | A | R | G | H | T | P M | GI 927211 |
| 465 | L | L | T | E | N | E | G | D | K | T | - | - | - | - | E | E | Q | V | S Y | GI 475198 |

DNA ENCODING A HISTAMINE H2 RECEPTOR

FIELD OF THE INVENTION

This invention relates to nucleic acid and amino acid sequences of a novel histamine H2 receptor and to the use of these sequences in the diagnosis, prevention, and treatment of various infectious and inflammatory conditions.

BACKGROUND OF THE INVENTION

Histamine is found in mast cells in all peripheral tissues. It is released via degranulation of mast cells as part of allergic and inflammatory responses to allergens, infection or trauma. Chronic inflammation can contribute to degradation of host tissue and will eventually lead to tissue destruction and to clinical disease associated with loss of organ function. Histamine is widely distributed in both neuronal and non-neuronal cells and has been implicated in a variety of CNS functions including arousal and analgesia.

In low concentrations, histamine mediates inflammation and allergies through the activation of the H1 receptor. The H1 receptor is widely distributed, regulates the contraction of smooth muscles of the intestine, trachea, bladder and blood vessels. The H1 receptor is also associated with the adrenal medulla, vascular endothelium, heart, cerebral cortex, cerebellum and spinal cord. In high concentrations, histamine regulates the release of gastric acid from parietal cells of the digestive system through activation of the histamine H2 receptor. The H2 receptor is found at high levels in heart and stomach and has limited distribution in smooth muscle, the uterus, and cells of the immune system. Both the H1 and the H2 receptors are seven transmembrane, G-protein coupled receptors (T7G).

T7G receptors are characterized by their seven hydrophobic domains which span the plasma membrane and form a bundle of antiparallel alpha helices. The transmembrane segments (TMS) are designated by roman numerals I to VII and account for structural and functional features of the receptor. In most cases, the bundle of helices forms a binding pocket; however, when the binding site must accommodate more bulky molecules, the extracellular N-terminal segment or one or more of the three extracellular loops participate in binding and in subsequent induction of conformational change in intracellular portions of the receptor. The activated receptor, in turn, interacts with an intracellular G-protein complex which mediates further intracellular signaling activities, generally interaction with guanine nucleotide binding (G) proteins and the production of second messengers such as cyclic AMP (cAMP), phospholipase C, inositol triphosphate or ion channel proteins.

The amino-terminus of the T7G is extracellular, of variable length and often glycosylated, while the carboxy-terminus is cytoplasmic and generally phosphorylated. Extracellular loops of the T7G alternate with intracellular loops and link the TMS. The most conserved domains of T7Gs are the transmembrane regions and the first two cytoplasmic loops. Taxonomic groups and their characteristics are reviewed in Bolander, F. F. (1994; Molecular Endocrinology, Academic Press, San Diego, Calif.), and some structural and functional information is summarized in Watson, S. and S. Arkinstall (1994; The G-Protein Linked Receptor Facts Book, Academic Press, San Diego, Calif.).

Much of the known information on histamine receptors, their conformations and activities is based on observations made following the administration of antagonists. For example, conventional antihistamines block the actions of histamine on smooth muscle of blood vessels, gut, or bronchi, but they do not inhibit histamine-stimulated gastric acid secretion. This observation led to further study of histamine receptors and the development of specific classes of antagonists for the different types of receptors. The conventional histamine receptor which is blocked by classic antihistamines is the known H-1 receptor whereas the gastric parietal cell or H-2 receptor (H2R) is not affected. H1 antagonists are used clinically in the treatment of allergic, asthmatic and anaphylactic reactions. The H2R antagonists are potent inhibitors of gastric acid secretion, exhibit some structural similarities to histamine and to each other, and are generally effective in healing and reducing the occurrence of gastric ulcers, particularly duodenal ulcers.

The H2R antagonist cimetidine, which shares the imidazole ring with histamine and bears a side chain containing a cyanoguanidine group, inhibits acid secretion by 70–80% and also reduces secretion in response to histamine, caffeine, insulin, hypoglycemia, and gastrin. Very few side effects are associated with cimetidine administration although slight and reversible increases in serum aminotransferase, creatinine, and serum prolactin levels are reported. Other inhibitors such as ranitidine, famotidine and nizatidine are about 6–10 times as potent as cimetidine in inhibiting gastric acid secretion and are also effective in the healing and prevention of duodenal ulcers. Structurally, ranitidine is a substituted aminomethylfuran, whereas famotidine and nizatidine have thiazole rings. As with cimetidine, a few mild side effects have been noted (Isselbacher, K. J. et al. (1994) Harrison's Principles of Internal Medicine, McGraw Hill, New York, N.Y.).

Evidence exists that several diseases may be caused by G protein and T7G mutations which cause either loss- or gain-of-function (Spiegel, A. M. (1995) Nature Med. 1:522–24). For example, a gain-of-function mutation of H2R which mimics the effects of excess histamine could actually cause disease. A recent report linked the knockout of the mouse G protein $\alpha i2$ gene to a lethal form of ulcerative colitis similar to the human disease. In this study, the mutation eventually led to development of adenocarcinoma in the mouse colon (Rudolph U. et. al. (1995) Nature Genet. 10:141–8).

The discovery of polynucleotides encoding novel histamine receptors, and the molecules themselves, presents the opportunity to investigate inflammatory conditions. Discovery of molecules related to histamine H2 receptors satisfies a need in the art by providing molecules which can be used to screen for and develop more effective antihistamines or other therapeutic compositions useful in the treatment of various infectious and inflammatory conditions.

SUMMARY OF THE INVENTION

The present invention features a novel histamine H2 receptor, hereinafter designated H2RH and characterized as having chemical and structural homology to histamine receptors. Accordingly, the invention features a substantially purified H2RH having the amino acid sequence, SEQ ID NO:1.

One aspect of the invention features isolated and substantially purified polynucleotides that encode H2RH. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode H2RH. The present invention also features antibodies which bind specifically to H2RH, and pharmaceutical compositions which modulate the activity of H2RH. The invention specifically features the identification and use of antagonists of H2RH.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of the novel histamine H2 inhibitor, H2RH. The alignment was produced using MacDNASIS PRO™ software (hitachi Software Engineering Co., Ltd., San Bruno, Calif.).

Figure 2A:
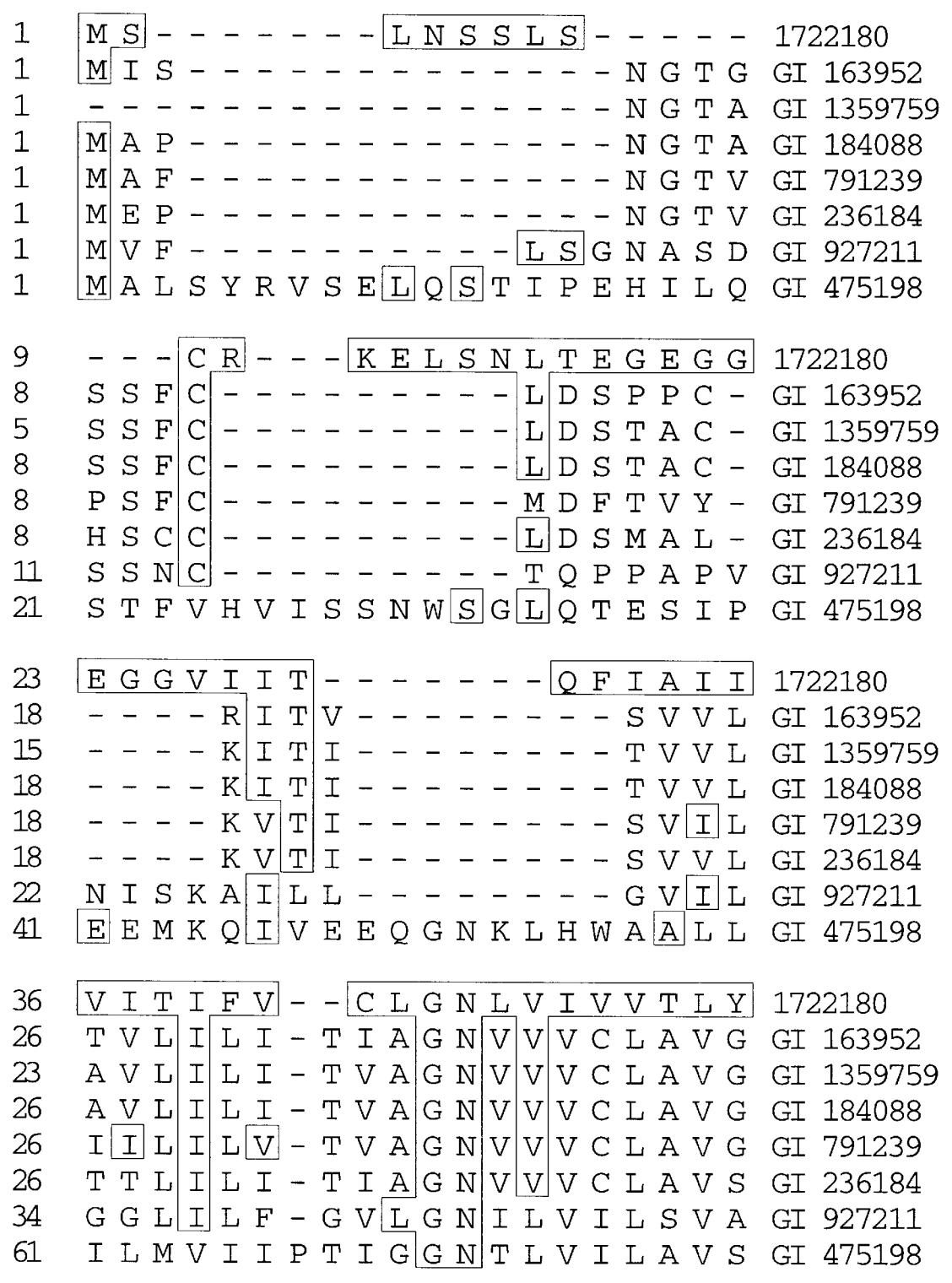
Figure 2B:
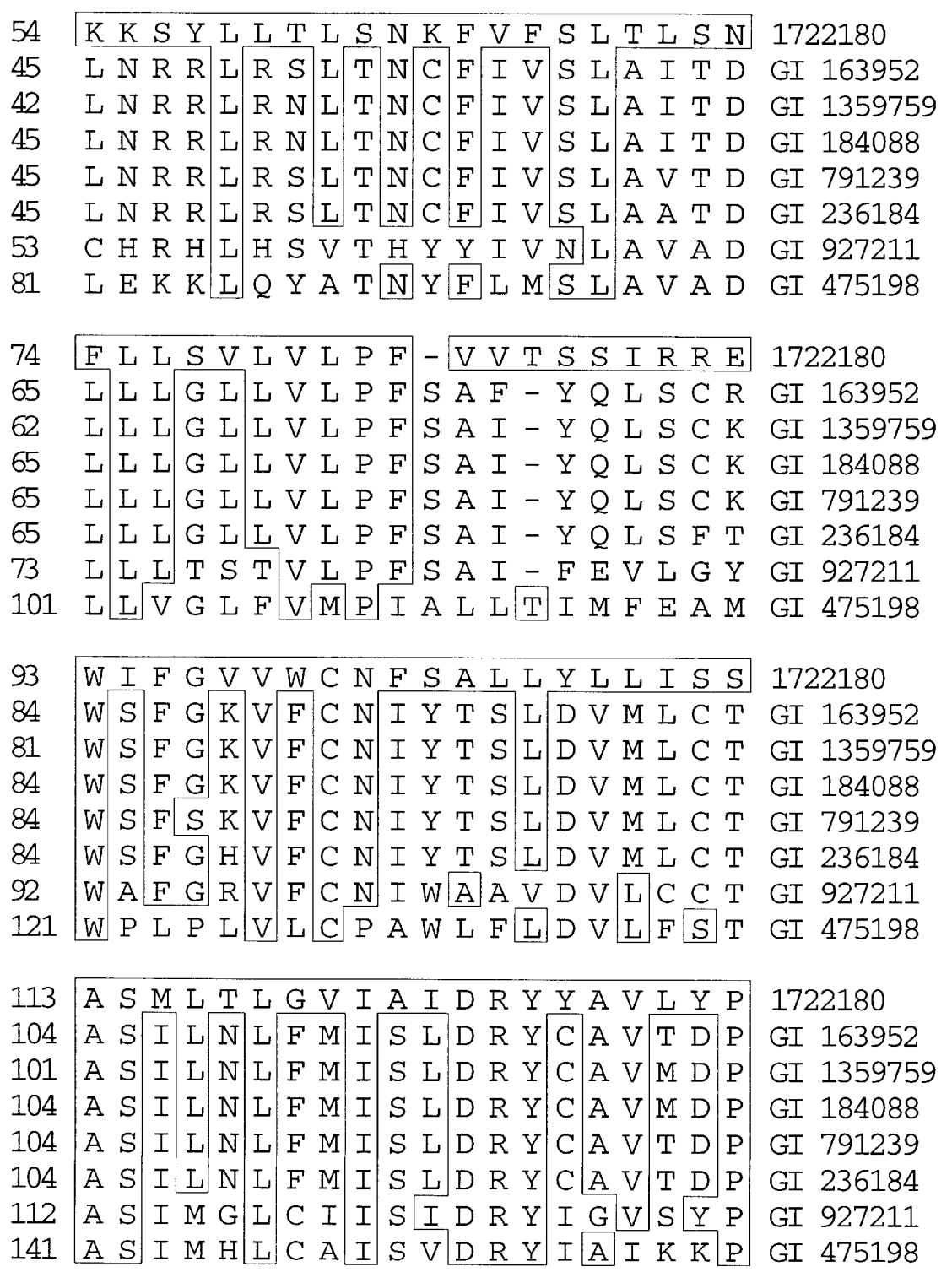
Figure 2C:
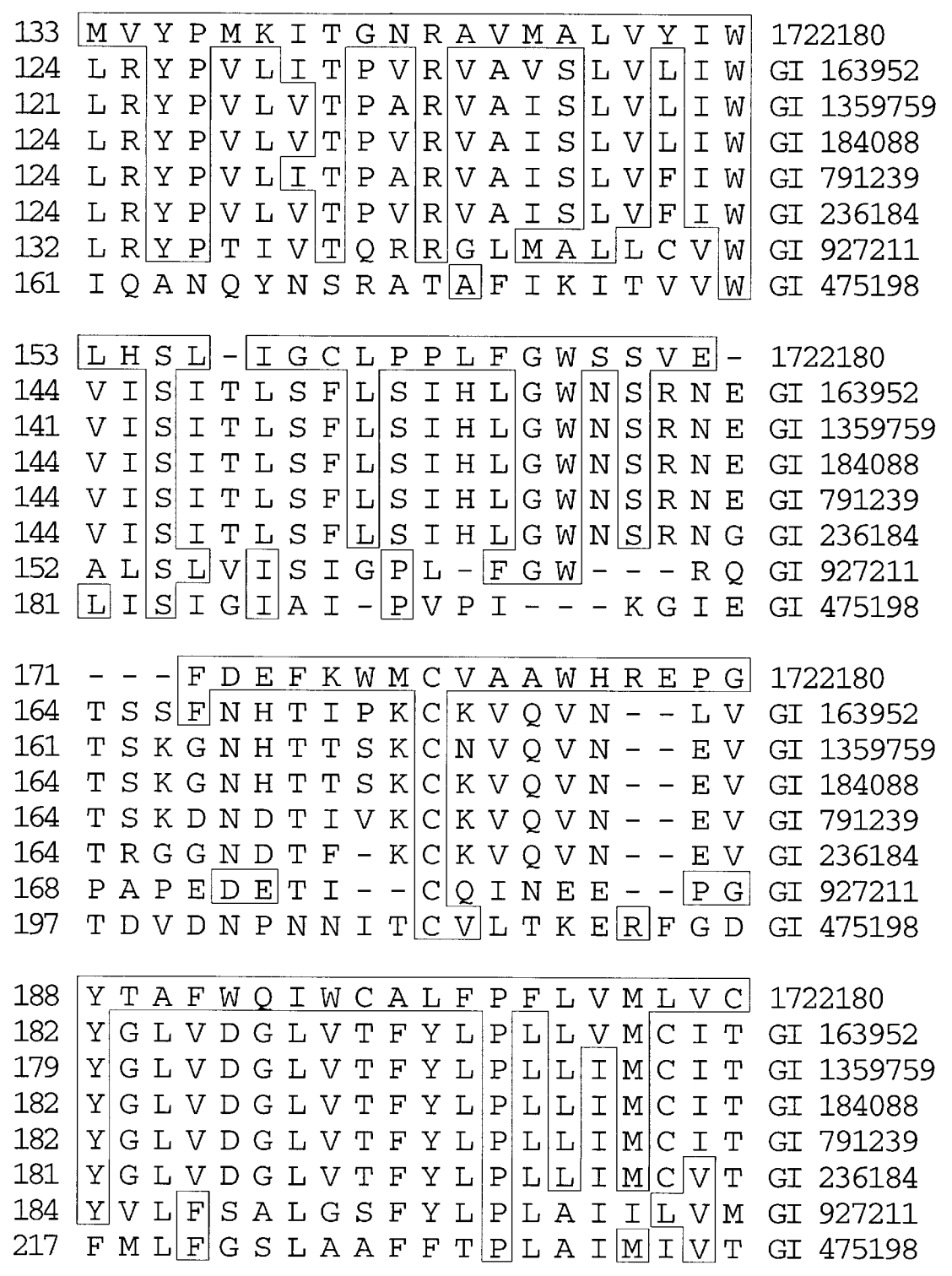
Figure 2D:
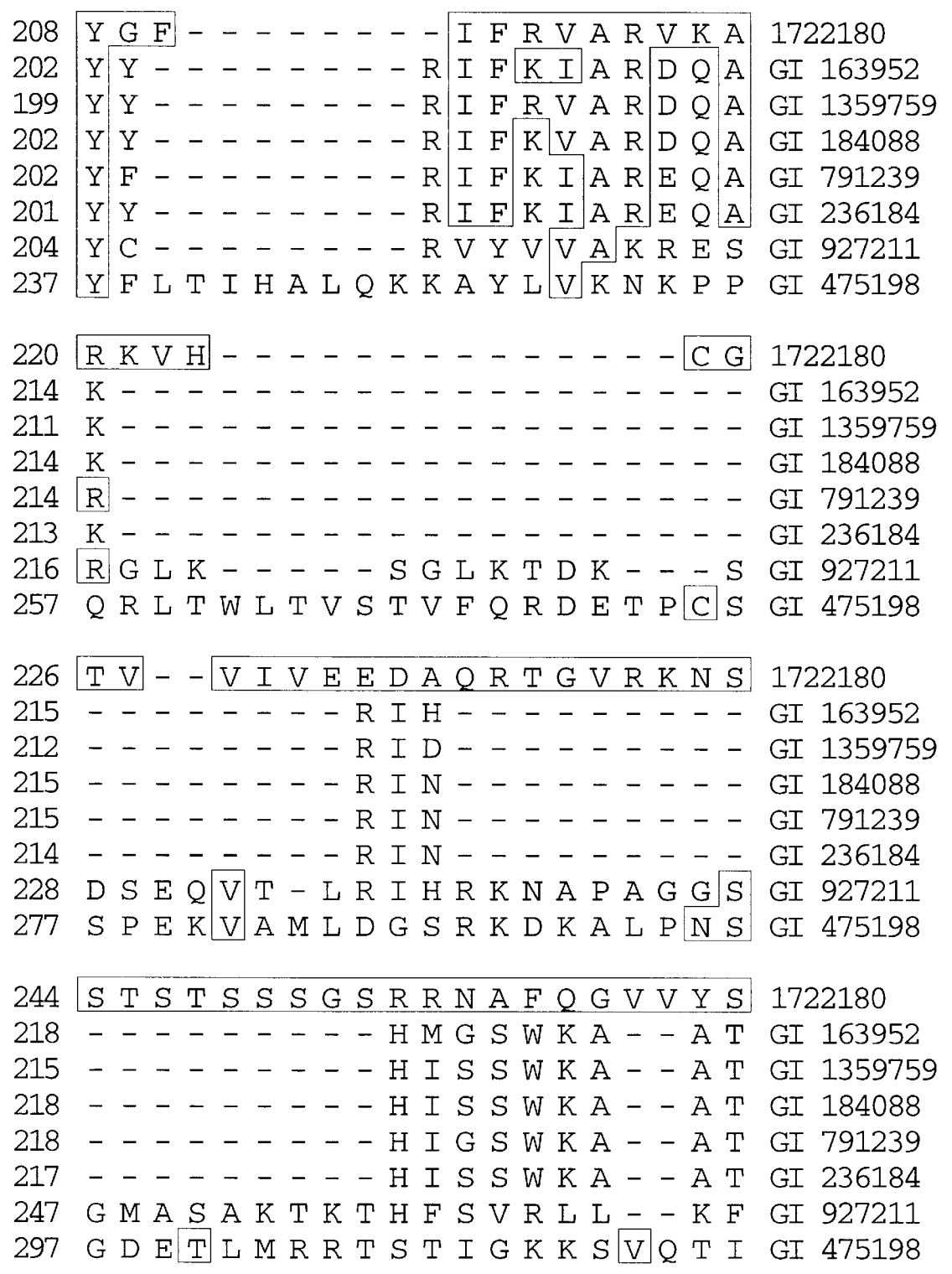
Figure 2E:
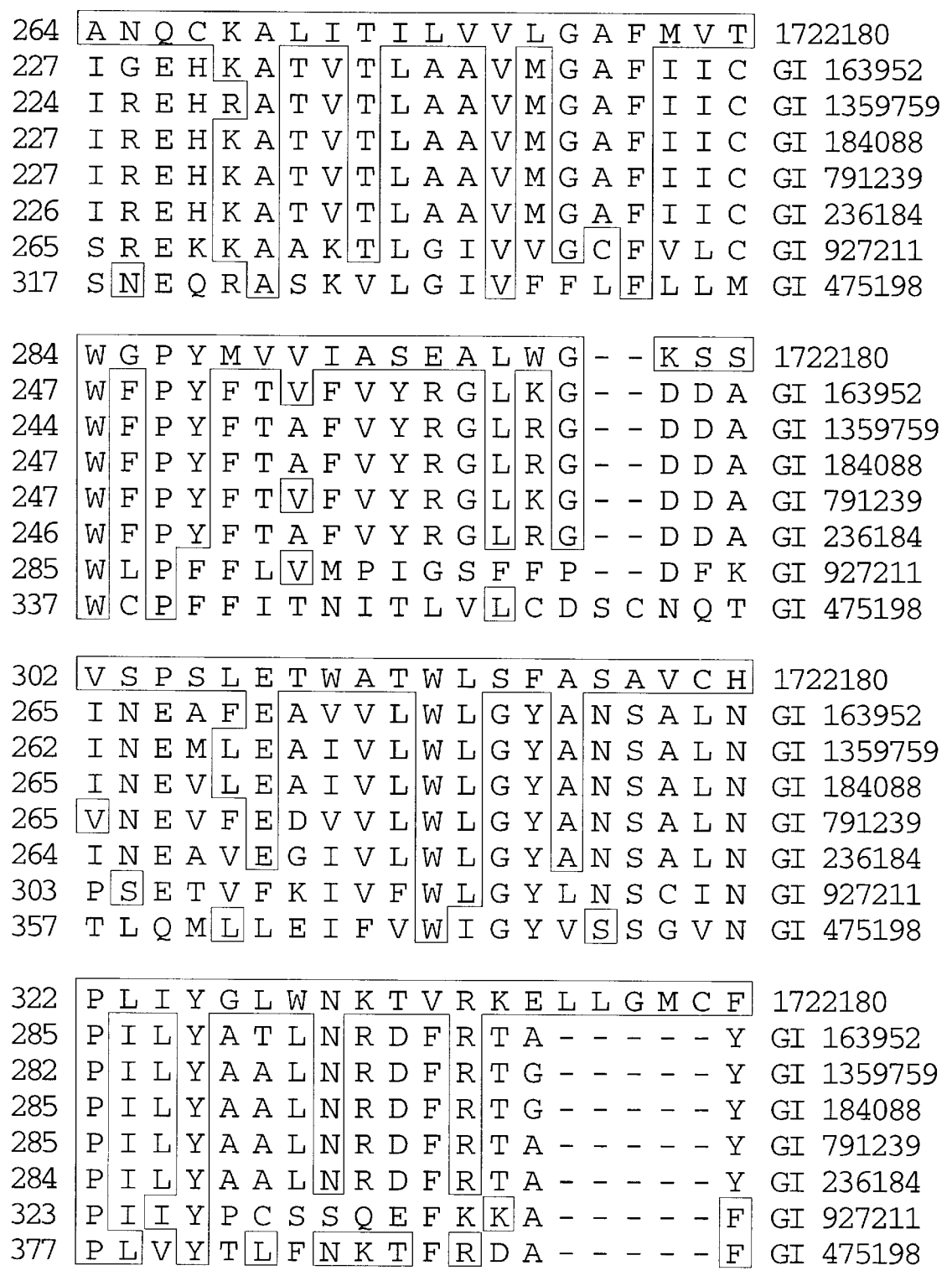
Figure 2G:
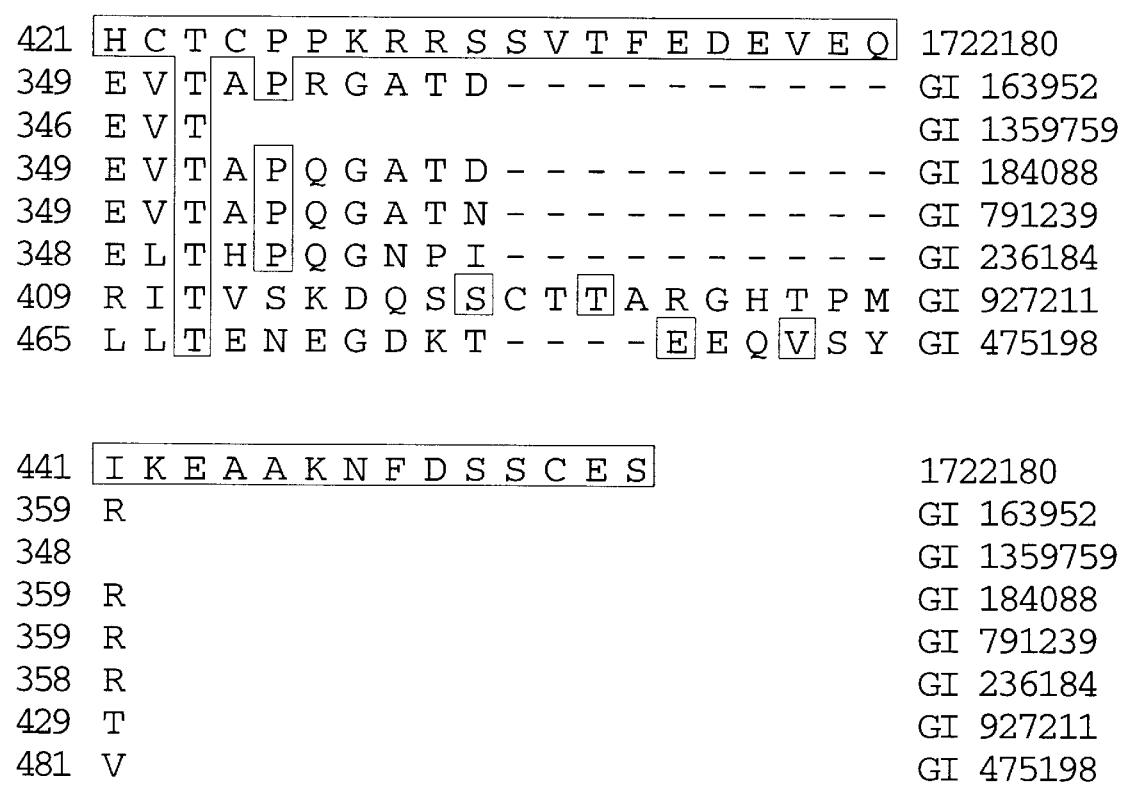

FIGS. 2A, 2B, 2C, 2D, 2E, 2F and 2G show the amino acid sequence alignments among H2RH (SEQ ID NO:1), canine H2R (GI 163952; SEQ ID NO:3), human H2R (GI 184088; SEQ ID NO:4), Cavia H2R (GI 791239; SEQ ID NO:5), rat H2R (GI 236184; SEQ ID NO:6), human alpha 1C adrenergic receptor (GI 927211; SEQ ID NO:7), and human 5-HT2B serotonin receptor (GI 475198; SEQ ID NO:8). The alignment was produced using the multisequence alignment program of DNASTAR™ software (DNASTAR Inc, Madison, Wis.).

DESCRIPTION OF THE INVENTION

Figure 3:
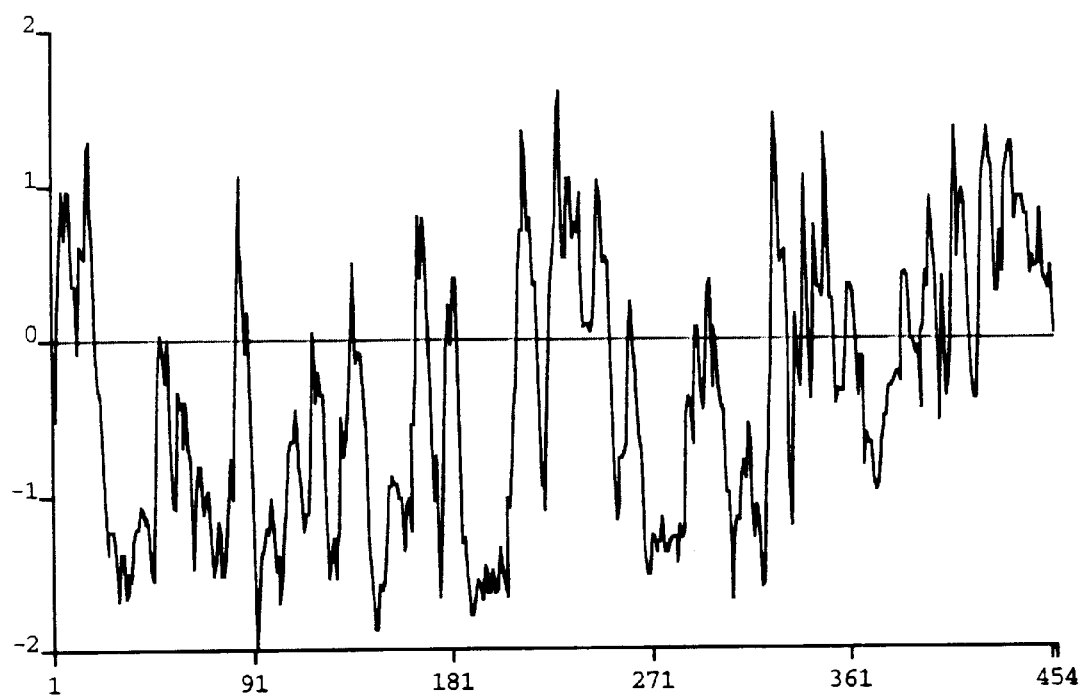
FIG. 3 shows the hydrophobicity plot (MacDNASIS PRO software) for H2RH, SEQ ID NO: 1; the positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.
Definitions "Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence", as used herein, refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

H2RH, as used herein, refers to the amino acid sequences of substantially purified H2RH obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of H2RH, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic H2RH, or any oligopeptide thereof, to induce a specific immune response in appropriate animals or cells and to bind with specific antibodies.

The term "agonist", as used herein, refers to a molecule which, when bound to H2RH, causes a change in H2RH which modulates the activity of H2RH. Agonists may include proteins, nucleic acids, carbohydrates, or any other molecules which bind to H2RH.

The terms "antagonist" or "inhibitor", as used herein, refer to a molecule which, when bound to H2RH, blocks or modulates the biological or immunological activity of H2RH. Antagonists and inhibitors may include proteins, nucleic acids, carbohydrates, or any other molecules which bind to H2RH.

The term "modulate", as used herein, refers to a change or an alteration in the biological activity of H2RH. Modulation may be an increase or a decrease in protein activity, a change in binding characteristics, or any other change in the biological, functional or immunological properties of H2RH.

The term "mimetic", as used herein, refers to a molecule, the structure of which is developed from knowledge of the structure of H2RH or portions thereof and, as such, is able to effect some or all of the actions of PE-60-like molecules.

The term "derivative", as used herein, refers to the chemical modification of a nucleic acid encoding H2RH or the encoded H2RH. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human H2RH and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given regions of the protein may induce structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding H2RH or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding H2RH in a sample and thereby correlates with expression of the transcript from the polynucleotide encoding the protein.

"Alterations" in the polynucleotide of SEQ ID NO:2, as used herein, comprise any alteration in the sequence of polynucleotides encoding H2RH including deletions, insertions, and point mutations that may be detected using hybridization assays. Included within this definition is the detection of alterations to the genomic DNA sequence which encodes H2RH (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding H2RH (e.g., using fluorescence in situ hybridization [FISH] to metaphase chromosomes spreads).

As used herein, the term "antibody" refers to intact molecules as well as fragments thereof, such as Fa, F(ab')$_2$, and Fv, which are capable of binding the epitopic determinant. Antibodies that bind H2RH polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of a novel histamine H2 receptor, (H2RH), the polynucleotides encoding H2RH, and the use of these compositions for the diagnosis, prevention, or treatment of infectious and inflammatory conditions or diseases, including but not limited to those of the cardiovascular, digestive, immune, respiratory, reproductive, urinary or central nervous systems.

The nucleic acid sequence encoding the human H2RH of the present invention is found in Incyte Clone 1722180 from the bladder cDNA library (BLADNOT06). A consensus sequence, SEQ ID NO:2, was derived from the extension and assembly of Incyte Clones 1278070 (SCORNOT03), 1722180 and 1722385 (BLADNOT06), and 1844864 (COLNNOT08). The sequence was first identified through a computer search of expressed sequences for amino acid sequence alignments.

In one embodiment, the invention encompasses the novel histamine H2 receptor, a polypeptide comprising the amino acid sequence of SEQ ID NO:1. H2RH is 454 amino acids in length and has a calculated molecular weight of 50587. Of five potential N-linked glycosylation sites, $N_4$ and $N_{15}$ are located in the extracellular portion of H2HR. The conserved residues of H2HR, $C_{100}$ and $C_{178}$, form a potential disulfide bridge and, $D_{124}RYYAV_{129}$, constitute a conserved G protein binding motif. The approximate locations of the TMS which define this molecule are: TMS1 contains the residues $Q_{30}$-$Y_{53}$; TMS2, $T_{70}$-$R_{90}$; TMS3, $F_{102}$-$I_{123}$; TMS4, $A_{144}$-$S_{168}$; TMS5, $E_{185}$-$F_{210}$; TMS6, $T_{272}$-$A_{295}$; and TMS7, $S_{305}$-$G_{326}$. The novel receptor has a $W_{192}$ substituting for the $D_{186}$ in TMS5; it has been suggested that the negatively charged residue in this position binds the positively charged imidazole ring of histamine. H2RH has two distinctive ATP binding motifs, $S_{293}$EALWGKS$_{300}$ and $G_{381}$GQPLGHS$_{388}$.

Figure 4:
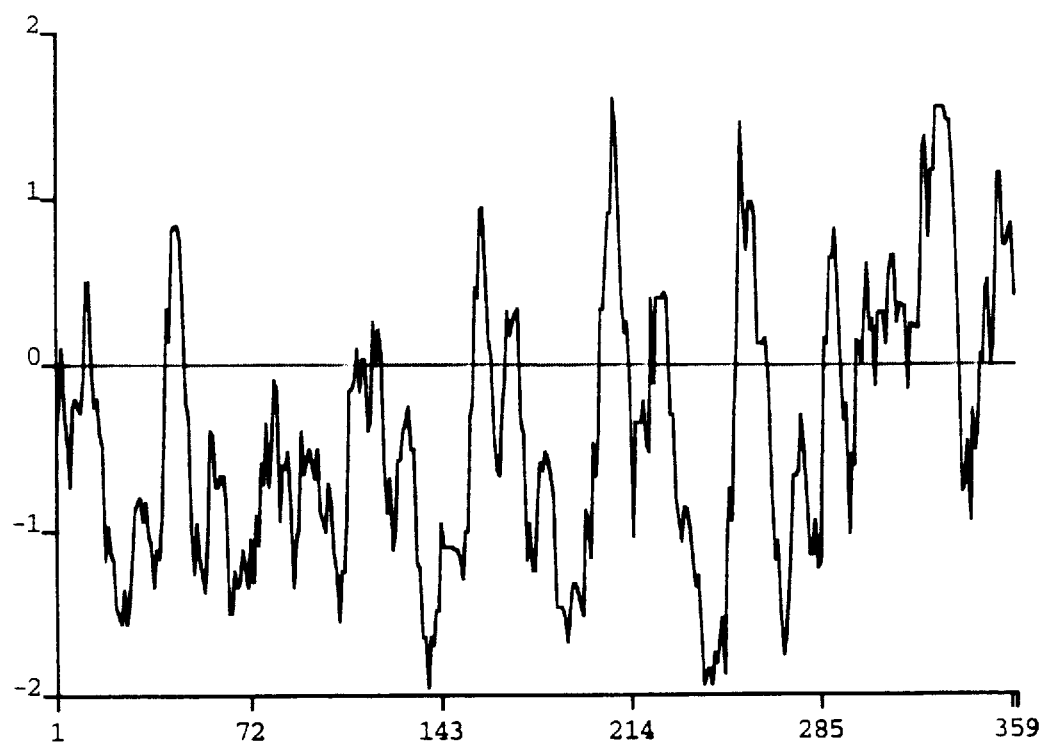
FIG. 4 shows the hydrophobicity plot for canine H2R, SEQ ID NO:3.

FIGS. 2A, 2B, 2C, 2D, 2E, 2F and 2G show the chemical and structural homology among H2RH, (SEQ ID NO:1), canine H2R (GI 163952; SEQ ID NO:3), human H2R (GI 184088; SEQ ID NO:4), Cavia H2R (GI 791239; SEQ ID NO:5), rat H2R (GI 236184; SEQ ID NO:6), human alpha 1C adrenergic receptor (GI 927211; SEQ ID NO:7), and human 5-HT2B serotonin receptor (GI 475198; SEQ ID NO:8). H2RH shares approximately 41% identity with the most closely related canine H2R (GI 163952; SEQ ID NO:3). As illustrated by FIGS. 3 and 4, H2RH and canine H2R have rather typical T7G hydrophobicity plots and their calculated isoelectric points are 7.98 and 9.19, respectively. Northern analysis (not shown) shows that H2RH is expressed only in the bladder (BLADNOT06), spinal cord (SCORNOT03), colon (COLNNOT08), and endothelial cells of the coronary artery (ENDONOT01) libraries.

The invention also encompasses H2RH variants. A preferred H2RH variant is one having at least 80%, and more preferably 90%, amino acid sequence similarity to the H2RH amino acid sequence (SEQ ID NO:1). A most preferred H2RH variant is one having at least 95% amino acid sequence similarity to SEQ ID NO:1.

The invention also encompasses polynucleotides which encode H2RH. Accordingly, any nucleic acid sequence which encodes the amino acid sequence of H2RH can be used to generate recombinant molecules which express H2RH. In a particular embodiment, the invention encompasses the polynucleotide comprising the nucleic acid sequence of SEQ ID NO:2 as shown in FIGS. 1A, 1B, 1C, 1D, and 1E.

It will be appreciated by those skilled in the art that as a result of the degeneracy of the genetic code, a multitude of nucleotide sequences encoding H2RH, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring H2RH, and all such variations are to be considered as being specifically disclosed.

Although nucleotide sequences which encode H2RH and its variants are preferably capable of hybridizing to the nucleotide sequence of the naturally occurring H2RH under appropriately selected conditions of stringency, it may be advantageous to produce nucleotide sequences encoding H2RH or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding H2RH and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode H2RH and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding H2RH or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding H2RH which are encompassed by the invention include deletions, insertions, or substitutions of different nucleotides resulting in a polynucleotide that encodes the same or a functionally equivalent H2RH. The encoded protein may also contain deletions, insertions, or substitutions of amino acid residues which produce a silent change and result in a functionally equivalent H2RH. Deliberate amino acid substitutions may be made on the basis of similarity in polarity, charge, solubility, hydrophobicity, hydrophilicity, and/or the amphipathic nature of the residues as long as the biological activity of H2RH is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding H2RH. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding H2RH may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode H2RH, or fusion proteins or functional equivalents thereof, may be used in recombinant DNA molecules to direct expression of H2RH in appropriate host cells. Due to the inherent degeneracy of the genetic code, other DNA sequences which encode substantially the same or a functionally equivalent amino acid sequence may be produced and these sequences may be used to clone and express H2RH.

As will be understood by those of skill in the art, it may be advantageous to produce H2RH-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter H2RH encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding H2RH may be ligated to a heterologous sequence to encode a fusion protein. For example, to screen peptide libraries for inhibitors of H2RH activity, it may be useful to encode a chimeric H2RH protein that can be recognized by a commercially available antibody. A fusion protein may also be engineered to contain a cleavage site located between the H2RH encoding sequence and the heterologous protein sequence, so that H2RH may be cleaved and purified away from the heterologous moiety.

In another embodiment, sequences encoding H2RH may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of H2RH, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W. H. Freeman and Co., New York, N.Y.). The composition of the synthetic peptides may be confirmed by amino acid analysis or sequencing (e.g., the Edman degradation procedure; Creighton, supra). Additionally, the amino acid sequence of H2RH, or any part thereof, may be altered during direct synthesis and/or combined using chemical methods with sequences from other proteins, or any part thereof, to produce a variant polypeptide.

In order to express a biologically active H2RH, the nucleotide sequences encoding H2RH or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding H2RH and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding H2RH. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding H2RH, vectors based on SV40 or EBV may be used with an appropriate selectable marker.

In bacterial systems, a number of expression vectors may be selected depending upon the use intended for H2RH. For example, when large quantities of H2RH are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding H2RH may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding H2RH may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express H2RH. For example, in one such system, *Autographa californica* nuclear polyhedrosis virus (AcNPV) is used as a vector to express foreign genes in *Spodoptera frugiperda* cells or in Trichoplusia larvae. The sequences encoding H2RH may be cloned into a non-essential region of the virus, such as the polyhedrin gene, and placed under control of the polyhedrin promoter. Successful insertion of H2RH will render the polyhedrin gene inactive and produce recombinant virus lacking coat protein. The recombinant viruses may then be used to infect, for example, *S. frugiperda* cells or Trichoplusia larvae in which H2RH may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding H2RH may be ligated into an adenovirus transcription/translation complex consisting of the late promoter and tripartite leader sequence. Insertion in a non-essential E1 or E3 region of the viral genome may be used to obtain a viable virus which is capable of expressing H2RH in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding H2RH. Such signals include the ATG initiation codon and adjacent sequences. In cases where sequences encoding H2RH, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express H2RH may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al.

(1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding H2RH is inserted within a marker gene sequence, recombinant cells containing sequences encoding H2RH can be identified by the absence of marker gene function. Alternatively, a marker gene can be placed in tandem with a sequence encoding H2RH under the control of a single promoter. Expression of the marker gene in response to induction or selection usually indicates expression of the tandem gene as well.

Alternatively, host cells which contain the nucleic acid sequence encoding H2RH and express H2RH may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding H2RH can be detected by DNA-DNA or DNA-RNA hybridization or amplification using probes or portions or fragments of polynucleotides encoding H2RH. Nucleic acid amplification based assays involve the use of oligonucleotides or oligomers based on the sequences encoding H2RH to detect transformants containing DNA or RNA encoding H2RH. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of H2RH, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on H2RH is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding H2RH include oligolabeling, nick translation, end-labeling or PCR amplification using a labeled nucleotide. Alternatively, the sequences encoding H2RH, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding H2RH may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode H2RH may be designed to contain signal sequences which direct secretion of H2RH through a prokaryotic or eukaryotic cell membrane. Other recombinant constructions may be used to join sequences encoding H2RH to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and H2RH may be used to facilitate purification. One such expression vector provides for expression of a fusion protein containing H2RH and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3:263–281) while the enterokinase cleavage site provides a means for purifying H2RH from the fusion protein. A discussion of vectors which contain fusion proteins is provided in Kroll, D. J. et al. (1993; DNA Cell Biol. 12:441–453).

In addition to recombinant production, fragments of H2RH may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of H2RH may be chemically synthesized separately and combined using chemical methods to produce the full length molecule.

Therapeutics

In another embodiment of the invention, H2RH may be used to screen drug libraries for antagonists which may be used therapeutically to block or modulate the activity of the receptor. Antagonists of H2RH may be used in any of those transient or chronic situations where inhibition is desirable. Such antagonists or inhibitors may be produced using methods which are generally known in the art, and include particularly the use of purified H2RH to produce antibodies or to screen libraries of pharmaceutical agents for those which specifically bind and inhibit the activities of H2RH.

For example, in one aspect, antagonists which specifically bind H2RH may be administered to the subject's gastric mucosa in conjunction with a suitable pharmaceutical carrier. Control of H2RH expression and activity may be used to treat duodenal ulcers and may be especially useful in combination with other therapeutic agents, such as the antacid and antibiotic regimes used to eliminate *Helicobacter pylori* and cure peptic ulcers. Reducing the amount of gastric acids secreted at mealtime as well as between meals will provide the time and a noncorrosive environment in which cells of the gastric mucosa can heal. In some cases, combinations of therapeutic agents having different cellular mechanisms of action and potentially synergistic effects will allow the use of lower effective doses of each agent with lessening side effects.

In another embodiment, antagonists of H2RH may be administered to the lungs of a subject in those cases in which the hyperactivity of H2RH is triggering allergic or asthmatic responses. In both responses, the ability to modulate H2HR activity may prevent the degranulation of excess numbers of monocytes, macrophages and other immune system cells that release the enzymes which produce unwarranted tissue destruction. Such therapy may also be warranted in the treatment of allergies, asthma, bronchitis, emphysema, aspergillosis, tuberculosis, and the like.

In another embodiment, antagonists of H2RH may be administered to a subject for the modulation of muscle spasms and cramping associated with gastric distress including but not limited to gastritis, flu, colitis, Crohn's disease and the like. Antagonists could also be employed to prevent the disorientation associated with motion sickness as well as the undue agitation associated with various conditions of the central nervous system including, but not limited to, diseases such as Alzheimer's disease, ataxia, Eaton-Lambert syndrome, epilepsy, myasthenia gravis, Parkinson's disease, and the like, or to conditions caused by the compression of brain or spinal tissues caused by tumors.

Since the novel H2RH was discovered in bladder and has a strong association with endothelial/epithelial tissues, antagonists may be administered to a subject to treat infections or inflammation of the urinary tract and bladder, and may administered to women with pelvic inflammatory disease with the intent of preventing infertility. In another embodiment, antagonists may be used to modulate H2RH in endothelial cells of the cardiovascular system and treat diseases such as arteriosclerosis, cardiomyopathy, endocarditis, ischemia, and the like.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with H2RH or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to H2RH have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of H2RH amino acids may be fused with those of another protein such as keyhole limpet hemocyanin and antibody produced against the chimeric molecule.

Monoclonal antibodies to H2RH may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce H2RH-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for H2RH may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between H2RH and its specific antibody. A two-site, monoclonal-based immunoassay utilizing monoclonal antibodies reactive to two non-interfering H2RH epitopes is preferred, but a competitive binding assay may also be employed (Maddox, supra).

In another embodiment of the invention, the polynucleotides encoding H2RH, or any fragment thereof, or antisense molecules, may be used for therapeutic purposes. In one aspect, antisense to the polynucleotide encoding H2RH may be used in situations in which it would be desirable to block the transcription of the mRNA. In particular, cells may be transformed with sequences complementary to polynucleotides encoding H2RH. Thus, antisense molecules may be used to modulate H2RH activity, or to achieve regulation of gene function. Such technology is now well known in the art, and sense or antisense oligomers or larger fragments, can be designed from various locations along the coding or control regions of sequences encoding H2RH.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding H2RH. These techniques are described both in Sambrook et al. (supra) and in Ausubel et al. (supra).

Genes encoding H2RH can be turned off by transforming a cell or tissue with expression vectors which express high levels of a polynucleotide or fragment thereof which encodes H2RH. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding H2RH, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding H2RH.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding H2RH. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of H2RH, antibodies to H2RH, mimetics, agonists, antagonists, or inhibitors of H2RH. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of H2RH, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example H2RH or fragments thereof, antibodies of H2RH, agonists, antagonists or inhibitors of H2RH, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind H2RH may be used for the diagnosis of conditions or diseases characterized by expression of H2RH, or in assays to monitor patients being treated with H2RH, agonists, antagonists or inhibitors. The antibodies useful for diagnostic purposes may be prepared in the same manner as those described above for therapeutics. Diagnostic assays for H2RH include methods which utilize the antibody and a label to detect H2RH in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring H2RH are known in the art and provide a basis for diagnosing altered or abnormal levels of H2RH expression. Normal or standard values for H2RH expression are established by combining body fluids or cell extracts taken from normal mammalian subjects, preferably human, with antibody to H2RH under conditions suitable for complex formation The amount of standard complex formation may be quantified by various methods, but preferably by photometric, means. Quantities of H2RH expressed in subject, control and disease, samples from biopsied tissues are compared with the standard values. Deviation between standard and subject values establishes the parameters for diagnosing disease.

In another embodiment of the invention, the polynucleotides encoding H2RH may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of H2RH may be correlated with disease. The diagnostic assay may be used to distinguish between absence, presence, and excess expression of H2RH, and to monitor regulation of H2RH levels during therapeutic intervention.

In one aspect, hybridization with PCR probes which are capable of detecting polynucleotide sequences, including genomic sequences, encoding H2RH or closely related molecules, may be used to identify nucleic acid sequences which encode H2RH. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding H2RH, alleles, or related sequences.

Probes may also be used for the detection of related sequences, and should preferably contain at least 50% of the nucleotides from any of the H2RH encoding sequences. The hybridization probes of the subject invention may be DNA or RNA and derived from the nucleotide sequence of SEQ ID NO:2 or from genomic sequence including promoter, enhancer elements, and introns of the naturally occurring H2RH.

Means for producing specific hybridization probes for DNAs encoding H2RH include the cloning of nucleic acid sequences encoding H2RH or H2RH derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding H2RH may be used for the diagnosis of any condition or disease which is associated with the expression and activity of H2RH. Examples of such conditions include, but are not limited to damage, disorders or diseases of the cardiovascular, digestive, immune, respiratory, reproductive, urinary or central nervous systems. The level at which H2RH is expressed or active in the endothelium of an artery or vein may correlate with the immune system interactions in arteriosclerosis and present an opportunity to diagnose those events. Similarly endothelial/epithelial and immune cell interations may be monitored in the lung, bladder, or gastric mucosa as they correlate with conditions or diseases affecting those structures.

The polynucleotide sequences encoding H2RH may be used in Southern or northern analysis, dot blot, or other membrane-based technologies; in PCR technologies; or in dip stick, pin, ELISA or chip assays utilizing fluids or tissues from patient biopsies to detect altered H2RH expression. Such qualitative or quantitative methods are well known in the art.

In a particular aspect, the nucleotide sequences encoding H2RH may be useful in assays that detect activation or induction of various cancers, particularly those mentioned above. The nucleotide sequences encoding H2RH may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding H2RH in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of H2RH, a normal or standard profile for expression is established. This may be accomplished by combining body fluids or cell extracts taken from normal subjects, either animal or human, with a sequence, or a fragment thereof, which encodes H2RH, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding H2RH may involve the use of PCR. Such oligomers may be chemically synthesized, generated enzymatically, or produced from a recombinant source. Oligomers will preferably consist of two nucleotide sequences, one with sense orientation (5'→3') and another with antisense (3'Λ5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of H2RH include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or calorimetric response gives rapid quantitation.

In another embodiment of the invention, the nucleic acid sequences which encode H2RH may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding H2RH on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, H2RH, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between H2RH and the agent being tested, may be measured.

Another technique for drug screening which may be used provides for high throughput screening of compounds having suitable binding affinity to the protein of interest as described in published PCT application WO84/03564. In this method, as applied to H2RH large numbers of different small test compounds are synthesized on a solid substrate, such as plastic pins or some other surface. The test compounds are reacted with H2RH, or fragments thereof, and washed. Bound H2RH is then detected by methods well known in the art. Purified H2RH can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding H2RH specifically compete with a test compound for binding H2RH. In this manner, the antibodies can be used to detect the presence of any peptide which shares one or more antigenic determinants with H2RH.

In additional embodiments, the nucleotide sequences which encode H2RH may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I BLADNOT06 cDNA Library Construction

The BLADNOT06 cDNA library was constructed from microscopically normal bladder tissue obtained from a 66-year-old Caucasian male. The normal and tumorous tissues were excised during a radical cystectomy for transitional cell carcinoma of the bladder. At the time of surgery, the patient was taking Dyazide® (SmithKline Beecham, Philadelphia, Pa.) and iron. Patient history included prostatic inflammatory disease, malignant neoplasm of the prostate, a transurethral prostatectomy, urinary diversion to the bowel, tobacco abuse, a lung neoplasm, and hypertension.

The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3M sodium acetate and 2.5 volumes of ethanol, resuspended in RNAse-free water, and DNase treated at 37° C. The RNA extraction was repeated with acid phenol pH 4.7 and precipitated with sodium acetate and ethanol as before. The mRNA was then isolated using the Qiagen Oligotex kit (QIAGEN; Chatsworth, Calif.) and used to construct the cDNA library.

The mRNA was handled according to the recommended protocols in the SuperScript Plasmid System for cDNA Synthesis and Plasmid Cloning (Cat. #18248-013; Gibco/BRL). The commercial plasmid pSPORT 1 (Gibco/BRL) was digested with EcoR I restriction enzyme (New England Biolabs, Beverley, Mass.). The overhanging ends of the plasmid were filled in using Klenow enzyme (New England Biolabs) and 2'-deoxynucleotide 5'-triphosphates (dNTPs). The plasmid was self-ligated and transformed into the bacterial host, E. coli strain JM 109. An intermediate plasmid produced by the bacteria failed to digest with EcoR I confirming the desired loss of the EcoR I restriction site.

This intermediate plasmid (pSPORT 1-ΔRI) was then digested with Hind III restriction enzyme (New England Biolabs) and the overhang was filled in with Klenow and dNTPs. A 10-mer linker of sequence 5' . . . CGGAATTCCG . . . 3' was phosphorylated and ligated onto the blunt ends. The product of the ligation reaction was digested with EcoR I and self-ligated. Following transformation into JM109 host cells, plasmids were isolated and screened for the digestibility with EcoR I but not with Hind III. A single colony which met this criteria was designated pINCY 1. The plasmid produced by this colony was sequenced and found to contain several copies of the 10-mer linker. These extra linkers did not present a problem as they were eliminated when the vector was prepared for cloning.

The plasmid was tested for its ability to incorporate cDNAs from a library prepared using Not I and EcoR I restriction enzymes. Several clones were sequenced and a single clone containing an insert of approximately 0.8 kb was selected to prepare a large quantity of the plasmid for library production. After digestion with Not I and EcoR I, the plasmid and the cDNA insert were isolated on an agarose gel and the vector was purified on a QIAQuick™ (QIAGEN, Chatsworth, Calif.) column for use in library construction.

cDNAs were fractionated on a Sepharose CL4B column (Cat. #275105-01; Pharmacia), and those cDNAs exceeding 400 bp were ligated into pSport I. The plasmid pSport I was subsequently transformed into DH5a™ competent cells (Cat. #18258-012; Gibco/BRL).

II Isolation and Sequencing of cDNA Clones

Plasmid DNA was released from the cells and purified using the REAL Prep 96 Plasmid Kit for Rapid Extraction Alkaline Lysis Plasmid Minipreps (Catalog #26173; QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, LIFE TECHNOLOGIES™) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems.

Most of the sequences disclosed herein were sequenced according to standard ABI protocols, using ABI kits (Cat. Nos. 79345, 79339, 79340, 79357, 79355). The solution volumes were used at 0.25×–1.0×concentrations. Some of the sequences disclosed herein were sequenced using different solutions and dyes which, unless otherwise noted, came from Amersham Life Science (Cleveland, Ohio).

First, stock solutions were prepared with HPLC water. The following solutions were each mixed by vortexing for 2 min: 1) Tris-EDTA (TE) Buffer was prepared by adding 49 ml water to 1 ml 50×Tris-EDTA concentrate, and 2) 10% Reaction Buffer was prepared by adding 45 ml water to 5 ml Concentrated Thermo Sequenase (TS) Reaction Buffer.

Second, 0.2 μM energy transfer (ET) primers were prepared in the following manner. Each primer tube was centrifuged prior to opening to assure that all primer powder was on the bottom of the tube. After each solubilization step, the mixture was vortexed for 2 min and then centrifuged for about 10 sec in a table-top centrifuge. 1 ml of 1×TE was added to each primer powder; adenine and cytosine dissolved primers (5-carboxyrhodamine-6G (R6G) and 6-carboxyfluorescein (FAM), respectively), were diluted with 9 ml 1×TE. Guanine and thymine dyes (N,N N',N"-tetramethyl-6-carboxyrhodamine (TAM) and 6-carboxy-X-rhodamine (ROX), respectively) were diluted with 19 ml 1×TE.

Next, the sequencing reaction ready mix was prepared as follows: 1) nucleotides A and C (8 ml of each) were added to 6 ml ET primer and 18 ml TS reaction buffer; and 2) nucleotides G and T (8 ml of each) were added to 6 ml ET primer and 18 ml TS reaction buffer.

After vortexing for 2 min and centrifuging for 20 sec, the resulting solution was divided into tubes in volumes of 8 ml per tube in order to make 1×(A,C) and 2×(G,T) solutions.

Prior to thermal cycling, each nucleotide was individually mixed with DNA template in the following proportions:

| Reagent | A (μL) | C (μL) | G (μL) | T (μL) |
|---|---|---|---|---|
| Reaction ready premix | 2 | 2 | 4 | 4 |
| DNA template | 1 | 1 | 2 | 2 |
| Total Volume | 3 | 3 | 6 | 6 |

These solutions undergo the usual thermal cycling:
1. Rapid thermal ramp to 94° C. (94° C. for 20 sec)*
2. Rapid thermal ramp to 50° C. (50° C. for 40 sec)*
3. Rapid thermal ramp to 68° C. (68° C. for 60 sec)*
* Steps 1, 2, and 3 were repeated for 15 cycles
4. Rapid thermal ramp to 94° C. (94° C. for 20 sec)**
5. Rapid thermal ramp to 68° C. (68° C. for 60 sec)**
** Steps 4 and 5 were repeated for 15 cycles
6. Rapid thermal ramp to 4° C. and hold until ready to combine.

After thermal cycling, the A, C, G, and T reactions with each DNA template were combined. Then, 50 μL 100% ethanol was added and the solution was spun at 4° C. for 30 min. The supernatant was decanted and the pellet was rinsed with 100 μL 70% ethanol. After being spun for 15 min the supernatant was discarded and the pellet was dried for 15 min under vacuum. The DNA sample was dissolved in 3 μL of formamide/50 mM EDTA. The resulting samples were loaded on wells in volumes of 2 μL per well for sequencing in ABI sequencers.

III Homology Searching of cDNA Clones and Their Deduced Proteins

Each cDNA was compared to sequences in GenBank using a search algorithm developed by Applied Biosystems and incorporated into the INHERIT™ 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding H2RH occurs. Abundance and percent abundance are also reported. Abundance directly reflects the number of times a particular transcript is represented in a cDNA library, and percent abundance is abundance divided by the total number of sequences examined in the cDNA library.

V Extension of Polynucleotides Encoding H2RH to Full Length or to Recover Regulatory Sequences Full length nucleic acid sequences encoding H2RH (SEQ ID NO:2) are used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQuick™ (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook et al., supra). After incubation for one hour at 37° C., the whole transformation mixture is plated on Luria Bertani (LB)-agar (Sambrook et al., supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer, and one or both of the gene specific primers used for the extension reaction are added to each well. Amplification is performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 μCi of [γ-$^{32}$P] adenosine triphosphate (Amersham) arid T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules to the H2RH-encoding sequence, or any part thereof, is used to inhibit in vivo or in vitro expression of naturally occurring H2RH. Although use of antisense oligonucleotides, comprising about 20 base-pairs, is specifically described, essentially the same procedure is used with larger cDNA fragments. An oligonucleotide based on the coding sequences of H2RH, as shown in FIGS. 1A, 1B, 1C, 1D, and 1E, is used to inhibit expression of naturally occurring H2RH. The complementary oligonucleotide is designed from the most unique 5' sequence as shown in FIGS. 1A, 1B, 1C, 1D, and 1E and used either to inhibit transcription by preventing promoter binding to the upstream nontranslated sequence or translation of an H2RH-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A, 1B, 1C, 1D and 1E.

VIII Expression of H2RH

Expression of H2RH is accomplished by subcloning the cDNAs into appropriate vectors and transforming the vectors into host cells. In this case, the cloning vector, pSport, previously used for the generation of the cDNA library is used to express H2RH in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of H2RH into the bacterial growth media which can be used directly in the following assay for activity.

IX Demonstration of H2RH Activity

Functional, cloned T7Gs may be expressed in heterologous expression systems and their biological activity assessed. One procedure for testing chimeric receptors is based on the procedure utilizing the $P_{2U}$ purinergic ($P_{2U}$) receptor as published by Erb, L. et al. (1993; Proc. Natl. Acad. Sci. 90:10449–53). Function of the chimeric receptor can easily be tested in cultured K562 human leukemia cells because these cells lack $P_{2U}$ receptors. K562 cells are transfected with expression vectors containing either normal or chimeric $P_{2U}$ and loaded with fura-a, fluorescent probe for $Ca^{++}$. Activation of properly assembled and functional extracellular H2RH-transmembrane/intracellular $P_{2U}$ receptors with extracellular UTP or ATP mobilizes intracellular $Ca^{++}$ which reacts with fura-a and is measured spectrofluorometrically. Bathing the transfected K562 cells in microwells containing appropriate ligands will trigger binding and fluorescent activity defining effectors of H2RH. Once ligand and function are established, the $P_{2U}$ system is useful for defining antagonists or inhibitors which block binding and prevent such fluorescent reactions.

An alternative procedure for testing H2RH activity utilizes the baculovirus expression system in Sf9 insect cells.

Insect cells are the perfect model system because no T7Gs have been identified in insects and G proteins are expressed at low levels. Additionally, Sf9 cells are capable of both the co-translational and post-translational processing events which facilitate receptor and G protein subunit interaction (Taussig, R. et al. (1994) Methods Enzymol. 238:95–108). Infection of the Sf9 cells with recombinant baculovirus containing H2RH results in cells with H2RH properly expressed and positioned in the cell membrane. Agonists and antagonists which specifically bind the receptor can be identified and measured using techniques well known in the art.

X Production of H2RH Specific Antibodies

H2RH that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring H2RH Using Specific Antibodies

Naturally occurring or recombinant H2RH is substantially purified by immunoaffinity chromatography using antibodies specific for H2RH. An immunoaffinity column is constructed by covalently coupling H2RH antibody to an activated chromatographic resin, such as CnBr-activated Sepharose (Pharmacia & Upjohn). After the coupling, the resin is blocked and washed according to the manufacturer's instructions.

Media containing H2RH is passed over the immunoaffinity column, and the column is washed under conditions that allow the preferential absorbance of H2RH (e.g., high ionic strength buffers in the presence of detergent). The column is eluted under conditions that disrupt antibody/H2RH binding (eg, a buffer of pH 2-3 or a high concentration of a chaotrope, such as urea or thiocyanate ion), and H2RH is collected.

XII Identification of Molecules Which Interact with H2RH

H2RH or biologically active fragments thereof are labeled with $^{251}$I Bolton-Hunter reagent (Bolton, A. E. and W. M. Hunter (1973) Biochem. J. 133:529–38). Candidate molecules previously arrayed in the wells of a multi-well plate are incubated with the labeled H2RH, washed and any wells with labeled H2RH complex are assayed. Data obtained using different concentrations of H2RH are used to calculate values for the number, affinity, and association of H2RH with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

What is claimed is:

1. An isolated and purified polynucleotide sequence encoding a histamine H2 receptor comprising the amino acid sequence of SEQ ID NO:1.

2. An isolated and purified polynucleotide sequence which is complementary to the polynucleotide sequence of claim 1.

3. An isolated and purified polynucleotide sequence comprising SEQ ID NO:2.

4. An isolated and purified polynucleotide sequence which is complementary to SEQ ID NO:2.

5. An expression vector containing the polynucleotide sequence of claim 1.

6. A host cell containing the vector of claim 5.

7. A method for producing a polypeptide comprising the amino acid sequence of SEQ ID NO:1 the method comprising the steps of:
  a) culturing the host cell of claim 6 under conditions suitable for the expression of the polypeptide; and
  b) recovering the polypeptide from the host cell culture.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 454 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: Consensus
        ( B ) CLONE: 1722180

( x i ) SEQUENCE DESCRIPTION: SEQ ID NO:1:

```
Met  Ser  Leu  Asn  Ser  Ser  Leu  Ser  Cys  Arg  Lys  Glu  Leu  Ser  Asn  Leu
 1             5                             10                         15

Thr  Glu  Gly  Glu  Gly  Gly  Glu  Gly  Gly  Val  Ile  Ile  Thr  Gln  Phe  Ile
             20                       25                       30

Ala  Ile  Ile  Val  Ile  Thr  Ile  Phe  Val  Cys  Leu  Gly  Asn  Leu  Val  Ile
         35                       40                       45
```

-continued

```
Val  Val  Thr  Leu  Tyr  Lys  Lys  Ser  Tyr  Leu  Leu  Thr  Leu  Ser  Asn  Lys
     50                  55                      60

Phe  Val  Phe  Ser  Leu  Thr  Leu  Ser  Asn  Phe  Leu  Leu  Ser  Val  Leu  Val
65                       70                  75                           80

Leu  Pro  Phe  Val  Val  Thr  Ser  Ser  Ile  Arg  Arg  Glu  Trp  Ile  Phe  Gly
               85                       90                            95

Val  Val  Trp  Cys  Asn  Phe  Ser  Ala  Leu  Leu  Tyr  Leu  Leu  Ile  Ser  Ser
               100                      105                      110

Ala  Ser  Met  Leu  Thr  Leu  Gly  Val  Ile  Ala  Ile  Asp  Arg  Tyr  Tyr  Ala
          115                      120                  125

Val  Leu  Tyr  Pro  Met  Val  Tyr  Pro  Met  Lys  Ile  Thr  Gly  Asn  Arg  Ala
     130                      135                      140

Val  Met  Ala  Leu  Val  Tyr  Ile  Trp  Leu  His  Ser  Leu  Ile  Gly  Cys  Leu
145                      150                      155                           160

Pro  Pro  Leu  Phe  Gly  Trp  Ser  Ser  Val  Glu  Phe  Asp  Glu  Phe  Lys  Trp
                    165                      170                      175

Met  Cys  Val  Ala  Ala  Trp  His  Arg  Glu  Pro  Gly  Tyr  Thr  Ala  Phe  Trp
                180                      185                      190

Gln  Ile  Trp  Cys  Ala  Leu  Phe  Pro  Phe  Leu  Val  Met  Leu  Val  Cys  Tyr
          195                      200                      205

Gly  Phe  Ile  Phe  Arg  Val  Ala  Arg  Val  Lys  Ala  Arg  Lys  Val  His  Cys
     210                      215                      220

Gly  Thr  Val  Val  Ile  Val  Glu  Glu  Asp  Ala  Gln  Arg  Thr  Gly  Val  Arg
225                           230                      235                      240

Lys  Asn  Ser  Ser  Thr  Ser  Thr  Ser  Ser  Ser  Gly  Ser  Arg  Arg  Asn  Ala
                    245                      250                      255

Phe  Gln  Gly  Val  Val  Tyr  Ser  Ala  Asn  Gln  Cys  Lys  Ala  Leu  Ile  Thr
               260                      265                      270

Ile  Leu  Val  Val  Leu  Gly  Ala  Phe  Met  Val  Thr  Trp  Gly  Pro  Tyr  Met
               275                      280                      285

Val  Val  Ile  Ala  Ser  Glu  Ala  Leu  Trp  Gly  Lys  Ser  Ser  Val  Ser  Pro
     290                      295                      300

Ser  Leu  Glu  Thr  Trp  Ala  Thr  Trp  Leu  Ser  Phe  Ala  Ser  Ala  Val  Cys
305                      310                      315                           320

His  Pro  Leu  Ile  Tyr  Gly  Leu  Trp  Asn  Lys  Thr  Val  Arg  Lys  Glu  Leu
               325                      330                      335

Leu  Gly  Met  Cys  Phe  Gly  Asp  Arg  Tyr  Tyr  Arg  Glu  Pro  Phe  Val  Gln
               340                      345                      350

Arg  Gln  Arg  Thr  Ser  Arg  Leu  Phe  Ser  Ile  Ser  Asn  Arg  Ile  Thr  Asp
          355                      360                      365

Leu  Gly  Leu  Ser  Pro  His  Leu  Thr  Ala  Leu  Met  Ala  Gly  Gly  Gln  Pro
     370                      375                      380

Leu  Gly  His  Ser  Ser  Thr  Gly  Asp  Thr  Gly  Phe  Ser  Cys  Ser  Gln
385                      390                      395                           400

Asp  Ser  Gly  Thr  Asp  Met  Met  Leu  Leu  Glu  Asp  Tyr  Thr  Ser  Asp  Asp
               405                      410                      415

Asn  Pro  Pro  Ser  His  Cys  Thr  Cys  Pro  Lys  Arg  Arg  Ser  Ser  Val
               420                      425                      430

Thr  Phe  Glu  Asp  Glu  Val  Glu  Gln  Ile  Lys  Glu  Ala  Ala  Lys  Asn  Phe
               435                      440                      445

Asp  Ser  Ser  Cys  Glu  Ser
          450
```

( 2 ) INFORMATION FOR SEQ ID NO:2:

(i) SEQUENCE CHARACTERISTICS:
    (A) LENGTH: 1584 base pairs
    (B) TYPE: nucleic acid
    (C) STRANDEDNESS: single
    (D) TOPOLOGY: linear (vii) IMMEDIATE SOURCE:
    (A) LIBRARY: Consensus
    (B) CLONE: 1722180

(xi) SEQUENCE DESCRIPTION: SEQ ID NO:2:

| | | | | | | |
|---|---|---|---|---|---|---|
| GGGACTGACT | AAATGTCAGC | AAGAGGAGAG | TCTCACCCTG | TTGCTTAGGC | AGATGGCGCG | 60 |
| ATCTCGGCTC | CTGGGTTCAA | GCAATTCTCC | TGCCTCAGCC | TCCTGAATAG | CCGGGATTAC | 120 |
| AGTCGTCCAG | CATGCTCTGC | CCACCCCACG | CCGAGGTGCA | CTGACCATGA | GCCTCAACTC | 180 |
| CTCCCTCAGC | TGCAGGAAGG | AGCTGAGTAA | TCTCACTGAG | GGGGAGGGTG | GCGAAGGGGG | 240 |
| CGTCATCATC | ACCCAGTTCA | TCGCCATCAT | TGTCATCACC | ATTTTTGTCT | GCCTGGGAAA | 300 |
| CCTGGTCATC | GTGGTCACCT | TGTACAAGAA | GTCCTACCTC | CTCACCCTCA | GCAACAAGTT | 360 |
| CGTCTTCAGC | CTGACTCTGT | CCAACTTCCT | GCTGTCCGTG | TTGGTGCTGC | CTTTTGTGGT | 420 |
| GACGAGCTCC | ATCCGCAGGG | AATGGATCTT | TGGTGTAGTG | TGGTGCAACT | TCTCTGCCCT | 480 |
| CCTCTACCTG | CTGATCAGCT | CTGCCAGCAT | GCTAACCCTC | GGGGTCATTG | CCATCGACCG | 540 |
| CTACTATGCT | GTCCTGTACC | CCATGGTGTA | CCCCATGAAG | ATCACAGGGA | ACCGGGCTGT | 600 |
| GATGGCACTT | GTCTACATCT | GGCTTCACTC | GCTCATCGGC | TGCCTGCCAC | CCTGTTTGG | 660 |
| TTGGTCATCC | GTGGAGTTTG | ACGAGTTCAA | ATGGATGTGT | GTGGCTGCTT | GGCACCGGGA | 720 |
| GCCTGGCTAC | ACGGCCTTCT | GGCAGATCTG | GTGTGCCCTC | TTCCCCTTTC | TGGTCATGCT | 780 |
| GGTGTGCTAT | GGCTTCATCT | TCCGCGTGGC | CAGGGTCAAG | GCACGCAAGG | TGCACTGTGG | 840 |
| CACAGTCGTC | ATCGTGGAGG | AGGATGCTCA | GAGGACCGGC | GTCCGGAAGA | ACTCCAGCAC | 900 |
| CTCCACCTCC | TCTTCAGGCA | GCAGGAGGAA | TGCCTTTCAG | GGTGTGGTCT | ACTCGGCCAA | 960 |
| CCAGTGCAAA | GCCCTCATCA | CCATCCTGGT | GGTCCTCGGT | GCCTTCATGG | TCACCTGGGG | 1020 |
| CCCCTACATG | GTTGTCATCG | CCTCTGAGGC | CCTCTGGGGG | AAAAGCTCCG | TCTCCCCGAG | 1080 |
| CCTGGAGACT | TGGGCCACAT | GGCTGTCCTT | TGCCAGCGCT | GTCTGCCACC | CCTGATCTA | 1140 |
| TGGACTCTGG | AACAAGACAG | TTCGCAAAGA | ACTACTGGGC | ATGTGCTTTG | GGGACCGGTA | 1200 |
| TTATCGGGAA | CCATTTGTGC | AACGACAGAG | GACTTCCAGG | CTCTTCAGCA | TTTCCAACAG | 1260 |
| GATCACAGAC | CTGGGCCTGT | CCCCACACCT | CACTGCGCTC | ATGGCAGGCG | GACAGCCCT | 1320 |
| GGGGCACAGC | AGCAGCACGG | GGGACACTGG | CTTCAGCTGC | TCCCAGGACT | CAGGGACAGA | 1380 |
| TATGATGCTG | CTTGAGGACT | ACACGTCTGA | TGACAACCCT | CCCTCTCACT | GCACTTGCCC | 1440 |
| ACCCAAGAGA | AGGAGCTCGG | TGACATTTGA | GGATGAAGTG | GAACAAATCA | AAGAAGCTGC | 1500 |
| CAAGAACTTC | GATTCTTCAT | GTGAAAGCTG | AAGTACACAA | GTCCTTGGAC | AGTTACGCAG | 1560 |
| CAAGCTTGGC | CAAAGCCATT | GAGG | | | | 1584 |

(2) INFORMATION FOR SEQ ID NO:3:

(i) SEQUENCE CHARACTERISTICS:
    (A) LENGTH: 359 amino acids
    (B) TYPE: amino acid
    (C) STRANDEDNESS: single
    (D) TOPOLOGY: linear (vii) IMMEDIATE SOURCE:
    (A) LIBRARY: GenBank
    (B) CLONE: 163952

( x i ) SEQUENCE DESCRIPTION: SEQ ID NO:3:

| | | | | | | | | | | | | | | |
|---|---|---|---|---|---|---|---|---|---|---|---|---|---|---|
| Met<br>1 | Ile | Ser | Asn | Gly<br>5 | Thr | Gly | Ser | Ser | Phe<br>10 | Cys | Leu | Asp | Ser | Pro<br>15 | Pro |
| Cys | Arg | Ile | Thr<br>20 | Val | Ser | Val | Val | Leu<br>25 | Thr | Val | Leu | Ile | Leu<br>30 | Ile | Thr |
| Ile | Ala | Gly<br>35 | Asn | Val | Val | Val | Cys<br>40 | Leu | Ala | Val | Gly | Leu<br>45 | Asn | Arg | Arg |
| Leu | Arg<br>50 | Ser | Leu | Thr | Asn | Cys<br>55 | Phe | Ile | Val | Ser | Leu<br>60 | Ala | Ile | Thr | Asp |
| Leu<br>65 | Leu | Leu | Gly | Leu<br>70 | Leu | Val | Leu | Pro | Phe<br>75 | Ser | Ala | Phe | Tyr | Gln | Leu<br>80 |
| Ser | Cys | Arg | Trp | Ser<br>85 | Phe | Gly | Lys | Val | Phe<br>90 | Cys | Asn | Ile | Tyr | Thr<br>95 | Ser |
| Leu | Asp | Val | Met<br>100 | Leu | Cys | Thr | Ala | Ser<br>105 | Ile | Leu | Asn | Leu | Phe<br>110 | Met | Ile |
| Ser | Leu | Asp<br>115 | Arg | Tyr | Cys | Ala | Val<br>120 | Thr | Asp | Pro | Leu | Arg<br>125 | Tyr | Pro | Val |
| Leu | Ile<br>130 | Thr | Pro | Val | Arg | Val<br>135 | Ala | Val | Ser | Leu | Val<br>140 | Leu | Ile | Trp | Val |
| Ile<br>145 | Ser | Ile | Thr | Leu | Ser<br>150 | Phe | Leu | Ser | Ile | His<br>155 | Leu | Gly | Trp | Asn | Ser<br>160 |
| Arg | Asn | Glu | Thr | Ser<br>165 | Ser | Phe | Asn | His | Thr<br>170 | Ile | Pro | Lys | Cys | Lys<br>175 | Val |
| Gln | Val | Asn | Leu<br>180 | Val | Tyr | Gly | Leu | Val<br>185 | Asp | Gly | Leu | Val | Thr<br>190 | Phe | Tyr |
| Leu | Pro | Leu<br>195 | Leu | Val | Met | Cys | Ile<br>200 | Thr | Tyr | Tyr | Arg | Ile<br>205 | Phe | Lys | Ile |
| Ala | Arg<br>210 | Asp | Gln | Ala | Lys | Arg<br>215 | Ile | His | His | Met | Gly<br>220 | Ser | Trp | Lys | Ala |
| Ala<br>225 | Thr | Ile | Gly | Glu | His<br>230 | Lys | Ala | Thr | Val | Thr<br>235 | Leu | Ala | Ala | Val | Met<br>240 |
| Gly | Ala | Phe | Ile | Ile<br>245 | Cys | Trp | Phe | Pro | Tyr<br>250 | Phe | Thr | Val | Phe<br>255 | Val | Tyr |
| Arg | Gly | Leu | Lys<br>260 | Gly | Asp | Asp | Ala | Ile<br>265 | Asn | Glu | Ala | Phe | Glu<br>270 | Ala | Val |
| Val | Leu | Trp<br>275 | Leu | Gly | Tyr | Ala | Asn<br>280 | Ser | Ala | Leu | Asn | Pro<br>285 | Ile | Leu | Tyr |
| Ala | Thr<br>290 | Leu | Asn | Arg | Asp | Phe<br>295 | Arg | Thr | Ala | Tyr | Gln<br>300 | Leu | Phe | Arg |
| Cys<br>305 | Arg | Pro | Ala | Ser | His<br>310 | Asn | Ala | Gln | Glu | Thr<br>315 | Ser | Leu | Arg | Ser | Asn<br>320 |
| Ser | Ser | Gln | Leu | Ala<br>325 | Arg | Asn | Gln | Ser | Arg<br>330 | Glu | Pro | Met | Arg | Gln<br>335 | Glu |
| Glu | Lys | Pro | Leu<br>340 | Lys | Leu | Gln | Val | Trp<br>345 | Ser | Gly | Thr | Glu | Val<br>350 | Thr | Ala |
| Pro | Arg | Gly | Ala<br>355 | Thr | Asp | Arg | | | | | | | | | |

( 2 ) INFORMATION FOR SEQ ID NO:4:

( i ) SEQUENCE CHARACTERISTICS:
        ( A ) LENGTH: 359 amino acids
        ( B ) TYPE: amino acid
        ( C ) STRANDEDNESS: single
        ( D ) TOPOLOGY: linear (vii) IMMEDIATE SOURCE:
    (A) LIBRARY: GenBank
    (B) CLONE: 184088

(xi) SEQUENCE DESCRIPTION: SEQ ID NO:4:

| Met | Ala | Pro | Asn | Gly | Thr | Ala | Ser | Ser | Phe | Cys | Leu | Asp | Ser | Thr | Ala |
|---|---|---|---|---|---|---|---|---|---|---|---|---|---|---|---|
| 1 | | | | 5 | | | | | 10 | | | | | 15 | |
| Cys | Lys | Ile | Thr | Ile | Thr | Val | Val | Leu | Ala | Val | Leu | Ile | Leu | Ile | Thr |
| | | | 20 | | | | 25 | | | | | 30 | | | |
| Val | Ala | Gly | Asn | Val | Val | Val | Cys | Leu | Ala | Val | Gly | Leu | Asn | Arg | Arg |
| | | 35 | | | | | 40 | | | | | 45 | | | |
| Leu | Arg | Asn | Leu | Thr | Asn | Cys | Phe | Ile | Val | Ser | Leu | Ala | Ile | Thr | Asp |
| | 50 | | | | | 55 | | | | | 60 | | | | |
| Leu | Leu | Leu | Gly | Leu | Leu | Val | Leu | Pro | Phe | Ser | Ala | Ile | Tyr | Gln | Leu |
| 65 | | | | | 70 | | | | | 75 | | | | | 80 |
| Ser | Cys | Lys | Trp | Ser | Phe | Gly | Lys | Val | Phe | Cys | Asn | Ile | Tyr | Thr | Ser |
| | | | | 85 | | | | | 90 | | | | | 95 | |
| Leu | Asp | Val | Met | Leu | Cys | Thr | Ala | Ser | Ile | Leu | Asn | Leu | Phe | Met | Ile |
| | | | 100 | | | | | 105 | | | | | 110 | | |
| Ser | Leu | Asp | Arg | Tyr | Cys | Ala | Val | Met | Asp | Pro | Leu | Arg | Tyr | Pro | Val |
| | | 115 | | | | | 120 | | | | | 125 | | | |
| Leu | Val | Thr | Pro | Val | Arg | Val | Ala | Ile | Ser | Leu | Val | Leu | Ile | Trp | Val |
| | | 130 | | | | | 135 | | | | | 140 | | | |
| Ile | Ser | Ile | Thr | Leu | Ser | Phe | Leu | Ser | Ile | His | Leu | Gly | Trp | Asn | Ser |
| 145 | | | | | 150 | | | | | 155 | | | | | 160 |
| Arg | Asn | Glu | Thr | Ser | Lys | Gly | Asn | His | Thr | Thr | Ser | Lys | Cys | Lys | Val |
| | | | | 165 | | | | | 170 | | | | | 175 | |
| Gln | Val | Asn | Glu | Val | Tyr | Gly | Leu | Val | Asp | Gly | Leu | Val | Thr | Phe | Tyr |
| | | | 180 | | | | | 185 | | | | | 190 | | |
| Leu | Pro | Leu | Leu | Ile | Met | Cys | Ile | Thr | Tyr | Tyr | Arg | Ile | Phe | Lys | Val |
| | | | 195 | | | | | 200 | | | | | 205 | | |
| Ala | Arg | Asp | Gln | Ala | Lys | Arg | Ile | Asn | His | Ile | Ser | Ser | Trp | Lys | Ala |
| | | 210 | | | | | 215 | | | | | 220 | | | |
| Ala | Thr | Ile | Arg | Glu | His | Lys | Ala | Thr | Val | Thr | Leu | Ala | Ala | Val | Met |
| 225 | | | | | 230 | | | | | 235 | | | | | 240 |
| Gly | Ala | Phe | Ile | Ile | Cys | Trp | Phe | Pro | Tyr | Phe | Thr | Ala | Phe | Val | Tyr |
| | | | | 245 | | | | | 250 | | | | | 255 | |
| Arg | Gly | Leu | Arg | Gly | Asp | Asp | Ala | Ile | Asn | Glu | Val | Leu | Glu | Ala | Ile |
| | | | 260 | | | | | 265 | | | | | 270 | | |
| Val | Leu | Trp | Leu | Gly | Tyr | Ala | Asn | Ser | Ala | Leu | Asn | Pro | Ile | Leu | Tyr |
| | | 275 | | | | | 280 | | | | | 285 | | | |
| Ala | Ala | Leu | Asn | Arg | Asp | Phe | Arg | Thr | Gly | Tyr | Gln | Gln | Leu | Phe | Cys |
| | 290 | | | | | 295 | | | | | 300 | | | | |
| Cys | Arg | Leu | Ala | Asn | Arg | Asn | Ser | His | Lys | Thr | Ser | Leu | Arg | Ser | Asn |
| 305 | | | | | 310 | | | | | 315 | | | | | 320 |
| Ala | Ser | Gln | Leu | Ser | Arg | Thr | Gln | Ser | Arg | Glu | Pro | Arg | Gln | Gln | Glu |
| | | | | 325 | | | | | 330 | | | | | 335 | |
| Glu | Lys | Pro | Leu | Lys | Leu | Gln | Val | Trp | Ser | Gly | Thr | Glu | Val | Thr | Ala |
| | | | 340 | | | | | 345 | | | | | 350 | | |
| Pro | Gln | Gly | Ala | Thr | Asp | Arg | | | | | | | | | |
| | | 355 | | | | | | | | | | | | | |

(2) INFORMATION FOR SEQ ID NO:5:

(i) SEQUENCE CHARACTERISTICS:
    (A) LENGTH: 359 amino acids (B) TYPE: amino acid
(C) STRANDEDNESS: single
(D) TOPOLOGY: linear (vii) IMMEDIATE SOURCE:
(A) LIBRARY: GenBank
(B) CLONE: 791239

(xi) SEQUENCE DESCRIPTION: SEQ ID NO:5:

```
Met Ala Phe Asn Gly Thr Val Pro Ser Phe Cys Met Asp Phe Thr Val
 1               5                  10                  15

Tyr Lys Val Thr Ile Ser Val Ile Leu Ile Ile Leu Ile Leu Val Thr
            20                  25                  30

Val Ala Gly Asn Val Val Cys Leu Ala Val Gly Leu Asn Arg Arg
        35                  40                  45

Leu Arg Ser Leu Thr Asn Cys Phe Ile Val Ser Leu Ala Val Thr Asp
    50                  55                  60

Leu Leu Leu Gly Leu Leu Val Leu Pro Phe Ser Ala Ile Tyr Gln Leu
65                  70                  75                  80

Ser Cys Lys Trp Ser Phe Ser Lys Val Phe Cys Asn Ile Tyr Thr Ser
                85                  90                  95

Leu Asp Val Met Leu Cys Thr Ala Ser Ile Leu Asn Leu Phe Met Ile
                100                 105                 110

Ser Leu Asp Arg Tyr Cys Ala Val Thr Asp Pro Leu Arg Tyr Pro Val
            115                 120                 125

Leu Ile Thr Pro Ala Arg Val Ala Ile Ser Leu Val Phe Ile Trp Val
        130                 135                 140

Ile Ser Ile Thr Leu Ser Phe Leu Ser Ile His Leu Gly Trp Asn Ser
145                 150                 155                 160

Arg Asn Glu Thr Ser Lys Asp Asn Asp Thr Ile Val Lys Cys Lys Val
                165                 170                 175

Gln Val Asn Glu Val Tyr Gly Leu Val Asp Gly Leu Val Thr Phe Tyr
            180                 185                 190

Leu Pro Leu Leu Ile Met Cys Ile Thr Tyr Phe Arg Ile Phe Lys Ile
        195                 200                 205

Ala Arg Glu Gln Ala Arg Arg Ile Asn His Ile Gly Ser Trp Lys Ala
    210                 215                 220

Ala Thr Ile Arg Glu His Lys Ala Thr Val Thr Leu Ala Ala Val Met
225                 230                 235                 240

Gly Ala Phe Ile Ile Cys Trp Phe Pro Tyr Phe Thr Val Phe Val Tyr
                245                 250                 255

Arg Gly Leu Lys Gly Asp Asp Ala Val Asn Glu Val Phe Glu Asp Val
            260                 265                 270

Val Leu Trp Leu Gly Tyr Ala Asn Ser Ala Leu Asn Pro Ile Leu Tyr
        275                 280                 285

Ala Ala Leu Asn Arg Asp Phe Arg Thr Ala Tyr His Gln Leu Phe Cys
    290                 295                 300

Cys Arg Leu Ala Ser His Asn Ser His Glu Thr Ser Leu Arg Leu Asn
305                 310                 315                 320

Asn Ser Gln Leu Asn Arg Ser Gln Cys Gln Glu Pro Arg Trp Gln Glu
                325                 330                 335

Asp Lys Pro Leu Asn Leu Gln Val Trp Ser Gly Thr Glu Val Thr Ala
            340                 345                 350

Pro Gln Gly Ala Thr Asn Arg
            355
```

( 2 ) INFORMATION FOR SEQ ID NO:6:

( i ) SEQUENCE CHARACTERISTICS:
        ( A ) LENGTH: 358 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 236184

( x i ) SEQUENCE DESCRIPTION: SEQ ID NO:6:

```
Met Glu Pro Asn Gly Thr Val His Ser Cys Cys Leu Asp Ser Met Ala
 1               5                  10                  15
Leu Lys Val Thr Ile Ser Val Val Leu Thr Thr Leu Ile Leu Ile Thr
            20                  25                  30
Ile Ala Gly Asn Val Val Cys Leu Ala Val Ser Leu Asn Arg Arg
        35                  40                  45
Leu Arg Ser Leu Thr Asn Cys Phe Ile Val Ser Leu Ala Ala Thr Asp
    50                  55                  60
Leu Leu Leu Gly Leu Leu Val Leu Pro Phe Ser Ala Ile Tyr Gln Leu
65                  70                  75                  80
Ser Phe Thr Trp Ser Phe Gly His Val Phe Cys Asn Ile Tyr Thr Ser
                85                  90                  95
Leu Asp Val Met Leu Cys Thr Ala Ser Ile Leu Asn Leu Phe Met Ile
                100                 105                 110
Ser Leu Asp Arg Tyr Cys Ala Val Thr Asp Pro Leu Arg Tyr Pro Val
            115                 120                 125
Leu Val Thr Pro Val Arg Val Ala Ile Ser Leu Val Phe Ile Trp Val
        130                 135                 140
Ile Ser Ile Thr Leu Ser Phe Leu Ser Ile His Leu Gly Trp Asn Ser
145                 150                 155                 160
Arg Asn Gly Thr Arg Gly Gly Asn Asp Thr Phe Lys Cys Lys Val Gln
                165                 170                 175
Val Asn Glu Val Tyr Gly Leu Val Asp Gly Leu Val Thr Phe Tyr Leu
                180                 185                 190
Pro Leu Leu Ile Met Cys Val Thr Tyr Tyr Arg Ile Phe Lys Ile Ala
            195                 200                 205
Arg Glu Gln Ala Lys Arg Ile Asn His Ile Ser Ser Trp Lys Ala Ala
    210                 215                 220
Thr Ile Arg Glu His Lys Ala Thr Val Thr Leu Ala Ala Val Met Gly
225                 230                 235                 240
Ala Phe Ile Ile Cys Trp Phe Pro Tyr Phe Thr Ala Phe Val Tyr Arg
                245                 250                 255
Gly Leu Arg Gly Asp Asp Ala Ile Asn Glu Ala Val Glu Gly Ile Val
            260                 265                 270
Leu Trp Leu Gly Tyr Ala Asn Ser Ala Leu Asn Pro Ile Leu Tyr Ala
        275                 280                 285
Ala Leu Asn Arg Asp Phe Arg Thr Ala Tyr Gln Gln Leu Phe His Cys
    290                 295                 300
Lys Phe Ala Ser His Asn Ser His Lys Thr Ser Leu Arg Leu Asn Asn
305                 310                 315                 320
Ser Leu Leu Pro Arg Ser Gln Ser Arg Glu Gly Arg Trp Gln Glu Glu
                325                 330                 335
Lys Pro Leu Lys Leu Gln Val Trp Ser Gly Thr Glu Leu Thr His Pro
            340                 345                 350
```

Gln Gly Asn Pro Ile Arg
            355

(2) INFORMATION FOR SEQ ID NO:7:

(i) SEQUENCE CHARACTERISTICS:
        (A) LENGTH: 429 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 927211

(xi) SEQUENCE DESCRIPTION: SEQ ID NO:7:

```
Met Val Phe Leu Ser Gly Asn Ala Ser Asp Ser Ser Asn Cys Thr Gln
 1               5                  10                  15

Pro Pro Ala Pro Val Asn Ile Ser Lys Ala Ile Leu Leu Gly Val Ile
             20                  25                  30

Leu Gly Gly Leu Ile Leu Phe Gly Val Leu Gly Asn Ile Leu Val Ile
             35                  40                  45

Leu Ser Val Ala Cys His Arg His Leu His Ser Val Thr His Tyr Tyr
 50                      55                  60

Ile Val Asn Leu Ala Val Ala Asp Leu Leu Leu Thr Ser Thr Val Leu
 65                      70                  75                  80

Pro Phe Ser Ala Ile Phe Glu Val Leu Gly Tyr Trp Ala Phe Gly Arg
                 85                  90                  95

Val Phe Cys Asn Ile Trp Ala Ala Val Asp Val Leu Cys Cys Thr Ala
             100                 105                 110

Ser Ile Met Gly Leu Cys Ile Ile Ser Ile Asp Arg Tyr Ile Gly Val
             115                 120                 125

Ser Tyr Pro Leu Arg Tyr Pro Thr Ile Val Thr Gln Arg Arg Gly Leu
 130                     135                 140

Met Ala Leu Leu Cys Val Trp Ala Leu Ser Leu Val Ile Ser Ile Gly
 145                     150                 155                 160

Pro Leu Phe Gly Trp Arg Gln Pro Ala Pro Glu Asp Glu Thr Ile Cys
                 165                 170                 175

Gln Ile Asn Glu Glu Pro Gly Tyr Val Leu Phe Ser Ala Leu Gly Ser
             180                 185                 190

Phe Tyr Leu Pro Leu Ala Ile Ile Leu Val Met Tyr Cys Arg Val Tyr
             195                 200                 205

Val Val Ala Lys Arg Glu Ser Arg Gly Leu Lys Ser Gly Leu Lys Thr
 210                     215                 220

Asp Lys Ser Asp Ser Glu Gln Val Thr Leu Arg Ile His Arg Lys Asn
 225                     230                 235                 240

Ala Pro Ala Gly Gly Ser Gly Met Ala Ser Ala Lys Thr Lys Thr His
                 245                 250                 255

Phe Ser Val Arg Leu Leu Lys Phe Ser Arg Glu Lys Lys Ala Ala Lys
             260                 265                 270

Thr Leu Gly Ile Val Val Gly Cys Phe Val Leu Cys Trp Leu Pro Phe
             275                 280                 285

Phe Leu Val Met Pro Ile Gly Ser Phe Phe Pro Asp Phe Lys Pro Ser
 290                     295                 300

Glu Thr Val Phe Lys Ile Val Phe Trp Leu Gly Tyr Leu Asn Ser Cys
 305                     310                 315                 320

Ile Asn Pro Ile Ile Tyr Pro Cys Ser Ser Gln Glu Phe Lys Lys Ala
                 325                 330                 335
```

| | | | | | | | | | | | | | | |
|---|---|---|---|---|---|---|---|---|---|---|---|---|---|---|
|Phe|Gln|Asn|Val|Leu|Arg|Ile|Gln|Cys|Leu|Arg|Arg|Lys|Gln|Ser|Ser|
| | | |340| | | |345| | | | |350| | |
|Lys|His|Ala|Leu|Gly|Tyr|Thr|Leu|His|Pro|Pro|Ser|Gln|Ala|Val|Glu|
| | |355| | | |360| | | | |365| | | |
|Gly|Gln|His|Lys|Asp|Met|Val|Arg|Ile|Pro|Val|Gly|Ser|Arg|Glu|Thr|
| |370| | | |375| | | | |380| | | | |
|Phe|Tyr|Arg|Ile|Ser|Lys|Thr|Asp|Gly|Val|Cys|Glu|Trp|Lys|Phe|Phe|
|385| | | | |390| | | | |395| | | | |400|
|Ser|Ser|Met|Pro|Arg|Gly|Ser|Ala|Arg|Ile|Thr|Val|Ser|Lys|Asp|Gln|
| | | | |405| | | | |410| | | |415| | |
|Ser|Ser|Cys|Thr|Thr|Ala|Arg|Gly|His|Thr|Pro|Met|Thr| | | |
| | | |420| | | | |425| | | | | | | |

( 2 ) INFORMATION FOR SEQ ID NO:8:

( i ) SEQUENCE CHARACTERISTICS:
        ( A ) LENGTH: 481 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 475198

( x i ) SEQUENCE DESCRIPTION: SEQ ID NO:8:

| | | | | | | | | | | | | | | | |
|---|---|---|---|---|---|---|---|---|---|---|---|---|---|---|---|
|Met|Ala|Leu|Ser|Tyr|Arg|Val|Ser|Glu|Leu|Gln|Ser|Thr|Ile|Pro|Glu|
|1| | | |5| | | | |10| | | | |15| |
|His|Ile|Leu|Gln|Ser|Thr|Phe|Val|His|Val|Ile|Ser|Ser|Asn|Trp|Ser|
| | | |20| | | | |25| | | | |30| | |
|Gly|Leu|Gln|Thr|Glu|Ser|Ile|Pro|Glu|Glu|Met|Lys|Gln|Ile|Val|Glu|
| | |35| | | | |40| | | | |45| | | |
|Glu|Gln|Gly|Asn|Lys|Leu|His|Trp|Ala|Ala|Leu|Leu|Ile|Leu|Met|Val|
| |50| | | | |55| | | | |60| | | | |
|Ile|Ile|Pro|Thr|Ile|Gly|Gly|Asn|Thr|Leu|Val|Ile|Leu|Ala|Val|Ser|
|65| | | | |70| | | | |75| | | | |80|
|Leu|Glu|Lys|Lys|Leu|Gln|Tyr|Ala|Thr|Asn|Tyr|Phe|Leu|Met|Ser|Leu|
| | | | |85| | | | |90| | | | |95| |
|Ala|Val|Ala|Asp|Leu|Leu|Val|Gly|Leu|Phe|Val|Met|Pro|Ile|Ala|Leu|
| | | |100| | | | |105| | | | |110| | |
|Leu|Thr|Ile|Met|Phe|Glu|Ala|Met|Trp|Pro|Leu|Pro|Leu|Val|Leu|Cys|
| | |115| | | | |120| | | | |125| | | |
|Pro|Ala|Trp|Leu|Phe|Leu|Asp|Val|Leu|Phe|Ser|Thr|Ala|Ser|Ile|Met|
| |130| | | | |135| | | | |140| | | | |
|His|Leu|Cys|Ala|Ile|Ser|Val|Asp|Arg|Tyr|Ile|Ala|Ile|Lys|Lys|Pro|
|145| | | | |150| | | | |155| | | | |160|
|Ile|Gln|Ala|Asn|Gln|Tyr|Asn|Ser|Arg|Ala|Thr|Ala|Phe|Ile|Lys|Ile|
| | | | |165| | | | |170| | | | |175| |
|Thr|Val|Val|Trp|Leu|Ile|Ser|Ile|Gly|Ile|Ala|Ile|Pro|Val|Pro|Ile|
| | | |180| | | | |185| | | | |190| | |
|Lys|Gly|Ile|Glu|Thr|Asp|Val|Asp|Asn|Pro|Asn|Asn|Ile|Thr|Cys|Val|
| | |195| | | | |200| | | | |205| | | |
|Leu|Thr|Lys|Glu|Arg|Phe|Gly|Asp|Phe|Met|Leu|Phe|Gly|Ser|Leu|Ala|
| |210| | | | |215| | | | |220| | | | |
|Ala|Phe|Phe|Thr|Pro|Leu|Ala|Ile|Met|Ile|Val|Thr|Tyr|Phe|Leu|Thr|
|225| | | | |230| | | | |235| | | | |240|
|Ile|His|Ala|Leu|Gln|Lys|Lys|Ala|Tyr|Leu|Val|Lys|Asn|Lys|Pro|Pro|

|  |  |  |  |  |  |  | 245 |  |  |  | 250 |  |  |  | 255 |  |
|---|---|---|---|---|---|---|---|---|---|---|---|---|---|---|---|---|
| Gln | Arg | Leu | Thr<br>260 | Trp | Leu | Thr | Val | Ser<br>265 | Thr | Val | Phe | Gln | Arg<br>270 | Asp | Glu |  |
| Thr | Pro | Cys<br>275 | Ser | Ser | Pro | Glu | Lys<br>280 | Val | Ala | Met | Leu | Asp<br>285 | Gly | Ser | Arg |  |
| Lys | Asp<br>290 | Lys | Ala | Leu | Pro | Asn<br>295 | Ser | Gly | Asp | Glu | Thr<br>300 | Leu | Met | Arg | Arg |  |
| Thr<br>305 | Ser | Thr | Ile | Gly | Lys<br>310 | Lys | Ser | Val | Gln | Thr<br>315 | Ile | Ser | Asn | Glu | Gln<br>320 |  |
| Arg | Ala | Ser | Lys | Val<br>325 | Leu | Gly | Ile | Val | Phe<br>330 | Phe | Leu | Phe | Leu | Leu<br>335 | Met |  |
| Trp | Cys | Pro | Phe<br>340 | Phe | Ile | Thr | Asn | Ile<br>345 | Thr | Leu | Val | Leu | Cys<br>350 | Asp | Ser |  |
| Cys | Asn | Gln<br>355 | Thr | Thr | Leu | Gln | Met<br>360 | Leu | Leu | Glu | Ile | Phe<br>365 | Val | Trp | Ile |  |
| Gly | Tyr<br>370 | Val | Ser | Ser | Gly | Val<br>375 | Asn | Pro | Leu | Val | Tyr<br>380 | Thr | Leu | Phe | Asn |  |
| Lys<br>385 | Thr | Phe | Arg | Asp | Ala<br>390 | Phe | Gly | Arg | Tyr | Ile<br>395 | Thr | Cys | Asn | Tyr | Arg<br>400 |  |
| Ala | Thr | Lys | Ser | Val<br>405 | Lys | Thr | Leu | Arg | Lys<br>410 | Arg | Ser | Ser | Lys | Ile<br>415 | Tyr |  |
| Phe | Arg | Asn | Pro<br>420 | Met | Ala | Glu | Asn | Ser<br>425 | Lys | Phe | Phe | Lys | Lys<br>430 | His | Gly |  |
| Ile | Arg | Asn<br>435 | Gly | Ile | Asn | Pro | Ala<br>440 | Met | Tyr | Gln | Ser | Pro<br>445 | Met | Arg | Leu |  |
| Arg | Ser<br>450 | Ser | Thr | Ile | Gln | Ser<br>455 | Ser | Ser | Ile | Ile | Leu<br>460 | Leu | Asp | Thr | Leu |  |
| Leu<br>465 | Leu | Thr | Glu | Asn | Glu<br>470 | Gly | Asp | Lys | Thr | Glu<br>475 | Glu | Gln | Val | Ser | Tyr<br>480 |  |
| Val |  |  |  |  |  |  |  |  |  |  |  |  |  |  |  |  |